l
US007371400B2

(12) United States Patent
Borenstein et al.

(10) Patent No.: US 7,371,400 B2
(45) Date of Patent: May 13, 2008

(54) MULTILAYER DEVICE FOR TISSUE ENGINEERING

(75) Inventors: Jeffrey T. Borenstein, Cambridge, MA (US); Kevin R. King, Cambridge, MA (US); Hidetomi Terai, Osaka (JP); Joseph P. Vacanti, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 302 days.

(21) Appl. No.: 10/038,891

(22) Filed: Jan. 2, 2002

(65) Prior Publication Data

US 2002/0182241 A1 Dec. 5, 2002

Related U.S. Application Data

(60) Provisional application No. 60/259,283, filed on Jan. 2, 2001.

(51) Int. Cl.
*A61F 2/00* (2006.01)
*C12N 11/02* (2006.01)
*C12N 11/08* (2006.01)
*C12N 5/06* (2006.01)
*C12N 5/08* (2006.01)

(52) U.S. Cl. .................. 424/423; 435/177; 435/180; 435/395

(58) Field of Classification Search ............... 424/423, 424/426, 93.7; 435/174, 177, 180, 182, 395
See application file for complete search history.

(56) References Cited

U.S. PATENT DOCUMENTS

| | | | |
|---|---|---|---|
| 5,061,620 A | 10/1991 | Tsukamoto et al. | |
| 5,204,055 A | 4/1993 | Sachs et al. | |
| 5,264,075 A * | 11/1993 | Zanini-Fisher et al. | ........ 438/53 |
| 5,486,359 A | 1/1996 | Caplan et al. | |
| 5,518,680 A * | 5/1996 | Cima et al. | .................. 264/401 |
| 5,843,780 A | 12/1998 | Thomson | |
| 5,849,553 A | 12/1998 | Anderson et al. | |
| 6,136,212 A * | 10/2000 | Mastrangelo et al. | ......... 216/49 |
| 6,139,574 A * | 10/2000 | Vacanti et al. | ............. 623/1.44 |
| 6,143,293 A | 11/2000 | Weiss et al. | |
| 6,165,486 A * | 12/2000 | Marra et al. | ................ 424/423 |
| 6,183,781 B1 | 2/2001 | Burke | |
| 6,200,802 B1 | 3/2001 | Greene et al. | |
| 6,245,566 B1 | 6/2001 | Gearhart et al. | |
| 6,455,311 B1 | 9/2002 | Vacanti | |

FOREIGN PATENT DOCUMENTS

| | | |
|---|---|---|
| WO | WO 96/40002 | 12/1996 |
| WO | WO 01/11011 | 2/2001 |

OTHER PUBLICATIONS

Bell et al., *Science* 221, 1052 (1981).
Burke, et al., *Ann Surg* 194, 413 (1981).
Langer, et al. *Science* 260, 920 (1993).
Vacanti, et al., Materials Research Society 252, 367 (1992).
Vacanti, et al., *Lancet* 354, 32 (1999).
Rennie, J. *Scientific American* 280, 37 (1999).
Lysaght, et al., *Tissue Eng* 4(3), 231 (1998).
Amedee et al. Differentiation, 58:157-164 (1994).
Compton, et al., *Laboratory Investigation* 60, 600 (1989).
Parenteau, et al., *Journal of Cellular Biochemistry* 45, 24 (1991).
Parenteau, et al., *Biotechnology and Bioengineering* 52, 3 (1996).
Purdue, et al., *J. Burn Care Rehab* 18, 52 (1997).
Hansbrough and Franco, *Clinical Plastic Surg* 25, 407 (1998).
Kane, et al., *Biomaterials* 20, 2363 (1999).
Griffith, et al., *Annals of Biomed. Eng.*, 26 (1998).
Griffith, et al., *Annals of Biomed. Eng.*, 831 (1997).
Folch, et al., Biotechnology Progress, 14, 388 (1998)).
Eiselt, et al., Biotechnol. Prog. 14, 134 (1998).
Wang et al, Nature Biotech 20, 602 (2002).
Runyan, et al., Semiconductor Integrated Circuit Processing Technology (Addison-Wesley Publishing Co., Reading MA 1990); Proceedings of the IEEE Micro Electro Mechanical Systems Conference 1987-1998.
Jansen, et al., "The Black Silicon Method IV: The Fabrication of Three-Dimensional Structures in Silicon with High Aspect Ratios for Scanning Probe Microscopy and Other Applications," IEEE Proceedings of Micro Electro Mechanical Systems Conference, pp. 88-93 (1995).
Frazier, et al., "Two dimensional metallic microelectrode arrays for extracellular stimulation and recording of neurons", IEEE Proceedings of the Micro Electro Mechanical Systems Conference, pp. 195-200 (1993).
Lehmann, "Porous Silicon—A New Material for MEMS", *IEEE Proceedings of the Micro Electro Mechanical Systems Conference*, pp. 1-6 (1996).
Laermer, et al., "Bosch Deep Silicon Etching: Improving Uniformity and Etch Rate for Advanced MEMS Applications," *Micro Electro Mechanical Systems*, Orlando, Fl, USA, (Jan. 17-21, 1999).
Despont, et al., "High-Aspect-Ratio, Ultrathick, Negative-Tone Near-UV Photoresist for MEMS", *Proc. of IEEE 10th Annual International Workshop on MEMS*, Nagoya, Japan, pp. 518-522 (Jan. 26-30, 1997)).
Henry, et al., "Micromachined Needles for the Transdermal Delivery of Drugs," *Micro Electro Mechanical Systems*, Heidelberg, Germany, pp. 494-498 (Jan. 26-29, 1998).
A.A. Ayon, S. Nagle, L. Frechette, A. Epstein and M.A. Schmidt, "Tailoring etch directionality in a deep reactive ion etching tool," *J. Vac. Sci. Tech.* B 18, 1412 (2000).

(Continued)

*Primary Examiner*—David M. Naff
(74) *Attorney, Agent, or Firm*—Edwards Angell Palmer & Dodge LLP; Peter C. Lauro, Esq.; George N. Chaclas, Esq.

(57) ABSTRACT

The invention provides for translating two-dimensional microfabrication technology into the third dimension. Two-dimensional templates are fabricated using high-resolution molding processes. These templates are then bonded to form three-dimensional scaffold structures with closed lumens. The scaffolds can serve as the template for cell adhesion and growth by cells that are added to the scaffolds through the vessels, holes or pores. These scaffolds can be formed by layering techniques, to interconnect flat template sheets to build up a fully vascularized organ.

50 Claims, 22 Drawing Sheets

OTHER PUBLICATIONS

Sachs, et al., *Manufacturing Review* 5, 117-126 (1992).
Ku, et al. *Nat. Biotechnol.*, 19, 971 (2001).
Keller, et al. (1999) *Exp. Hematol.* 27:777-787.
Marti, et al. (1995) *Nature.* 375:322-325.
Prelle, et al. (2000) *Biochem. Biophy. Res. Commun.* 277:631-638.
Hardt, et al. (1985) *Eur. J. Immunol.* 15:472-478.
Huelsken, et al. (2001) *Cell.* 105:533-545.
Ji, et al. (2000) *J. Bone Miner. Metab.* 18:132-139.
Migliorati, et al. (1987) *J. Immunol.* 138:3618-3625.
Eghbali, et al. (1991) *Proc. Natl. Acad. Sci. USA.* 88:795-799.
Niijima, et al. (1995) *J. Neurosci.* 15:1180-1194.
Guo, et al. (1997) *Dev. Biol.* 184:61-69.
Ling, et al. (1998) *Exp. Neurol.* 149:411-423.
Lopez-Fernandez, et al. (2000) *J. Biol. Chem.* 275:21653-60.
Wang, et al. (1989) *Leuk. Res.* 13:1091-1097.
Lako, et al. (2001) *Mech. Dev.* 103:49-59.
Evans et al. (1981) Nature 292:154-156.
Matsui et al. (1991) Nature 353:750-2.
Thomson et al. (1995) Proc. Natl. Acad. Sci. USA. 92:7844-8.
Thomson et al. (1998) Science 282:1145-1147.
Shamblott et al. (1998) Proc. Natl. Acad. Sci. USA 95:13726-31.
Mitaka, et al., *Biochem Biophys Res Commun* 214, 310 (1995).
Taneto, et al. *Am Jpathol* 148, 383 (1996).
Mitaka, et al., *Hepatology* 29, 111 (1999).
Teebken, et al., *Eur J. Vasa Endovasc. Surg.* 19, 381 (2000).
Ranucci, et al., *Biomaterials* 21, 783 (2000).
Burg et al., *J. Biomed. Mater. Res* 51, 642 (2000).
Jo et al., *SPIE* 3877, 222 (1999).
Camporese, et al., *IEEE Electron. Device Lett. EDL* 2, 61(1981).
Block, et al., *J Cell Biol*, 132, 1133 (1996).
Landry, et al., *J Cell Biol*, 101, 914 (1985).
Nishikawa, et al., *Exp Cell Res*, 223, 357 (1996).
Uyama, et al., *Transplantation* 55, 932 (1993).
Den Braber, et al. *J. Biomed. Mater. Res.* 40, 291 (1998).
Aiken, et al., *J Pediatr Surg* 25, 140 (1990).
Seglen, *Methods Cell Biol* 13, 29 (1976).
Schwerer, et al., *Clinica Chemica Acta* 163, 237 (1987).
Peterson JE *J Pathol Bacteriol* 89, 153 (1965).
Duffy, et al., *Anal. Chem.* 70, 4974 (1998).
Mitaka, et al., *Gastroenterol Hepatol* 13 Suppl. S70 (1998).
Tateno, et al., *Am J Pathol* 149, 1593 (1996).
Laconi, et al., *Am J. Pathol* 153, 319 (1998).
Hansborough & Franco (1998) "Skin Replacements," Clin. Plast. Surg. 25(3): 407-23.
Henry, et al. (1998) "Micromachined Needles for the Transdermal Delivery of Drugs," The Eleventh Annual International Workshop on Micro Electro Mechanical Systems, Heidelberg, Germany, Jan. 25-29, 1998.
Kourepenis et al. (1998) "Performance of MEMS Inertial Sensors," Position Location and Navigation Symposium, Aerospace & Electronic Systems Society, Palm Springs, California, Apr. 20-23, 1996.
McWhorter et al. (1997) "Vol. 2: Micromachining and Trends for the Twenty-First Century," Handbook of Microlithography, Micromachinery and Microfabrication. Ed. P. Rai-Choudhury, Bellingham, WA: SPIE Press.
Rennie, J. ed. (1999) Special Report: The promise of tissue Engineering. Scientific American 280: 37.
Vacanti et al. (1992) "Tissue-Inducing Biomaterials," Materials Research Society Symposium Proceedings 252: 367.
Langer & Vacanti, (1993) "Tissue Engineering," Science 260(5110): 920-6.
Langer & Vacanti, (1999) "Tissue Engineering: The obstacles to building new organs from cells and synthetic polymers are daunting but surmountable," Scientific American 280, 86-89.
Sunback & Vacanti, "Alternatives to liver transplantation: Fromhepatocyte transplantation to tissue-engineered organs," Gastroenterology 118: 438-442 (2000).
Kaihara, et al: "Silicon micromachining to tissue engineer branched vascular channels for liver fabrication", Tissue Engineering, Apr. 2002, vol. 6, No. 2, Apr. 2000, pp. 105-117.

* cited by examiner

1. Start Substrate Wafer

2. Deposit Masking Material

3. Pattern Masking Material

4. Etch Substrate Wafer

MICROFABRICATION PROCESS

MULTI-DEPTH MICROFABRICATION PROCESS.

SCAFFOLD FABRICATION PROCESS FROM MOLDS

VASCULAR PATTERN OF TEP-0

VASCULAR PATTERN OF TEP-1

VASCULAR PATTERN OF TEP-2a

CHANNEL FORMED BY OPTIMIZED PLASMA ETCHING

ANGLED SIDEWALL PRODUCED BY KOH ETCHING

SHARP CURVES AND CORNERS DUE TO ETCH BEHAVIOR
AT INTERSECTIONS BETWEEN CHANNELS

NEGATIVE MOLD WITH CHANNELS RAISED

SCANNING ELECTRON MICROGRAPH OF
VARIED-WIDTH AND VARIED-HEIGHT CHANNELS

MICROMACHINED UNIT WITH THROUGH-HOLE

SET MICROMACHINED UNITS WITH THROUGH-HOLES

SCAFFOLD WITH SET OF MICROMACHINED UNITS, THROUGH-HOLES AND
CHANNELS

SCAFFOLD WITH THROUGH-HOLES

STACKING OF SCAFFOLD WITH THROUGH-HOLES AND SCAFFOLD WITH SET OF
MICROMACHINED UNITS, THROUGH-HOLES AND CHANNELS

FOLDING METHOD FOR FORMING A THREE-DIMENSIONAL POLYMER SCAFFOLD

ALBUMIN PRODUCTION

STRIATED STACKED SCAFFOLD SYSTEM

STRIATED STACKED SCAFFOLD SYSTEM

STRIATED STACKED SCAFFOLD SYSTEM

STRIATED STACKED SCAFFOLD SYSTEM

MULTILAYER DEVICE FOR TISSUE ENGINEERING

CLAIM OF PRIORITY

This application claims priority to U.S. provisional patent application Ser. No. 60/259,283; filed Jan. 2, 2001.

GOVERNMENT INTERESTS

Some of the work described herein was sponsored by the Department of the Army, Cooperative Agreement DAMD-99-2-9001. The U.S. Government has certain rights in this invention.

FIELD OF THE INVENTION

The invention relates generally to tissue engineering. Specifically, this invention provides a technique for fabricating three-dimensional vascularized tissues for transplantation in human recipients.

BACKGROUND OF THE INVENTION

Vital organ failure is one of the most critical problems facing the health care field today. In the United States, the number of patients awaiting an organ for transplant has risen above 75,000. Despite advances in living donor organ transplantation, a severe shortage of donor organs available to these patients remains as the crux of the problem. Mechanical devices are one approach to addressing the organ shortage. Xenografts are another approach. However, due to the intrinsic limitations of these technologies, these approaches are only partial solutions to the problem.

Tissue engineering can be a complete and permanent solution to the problem of organ loss or failure, but the primary challenge for tissue engineering vital organs is the requirement for a vascular supply for nutrient and metabolite transfer. To date, tissue engineering has relied on the ingrowth of blood vessels into tissue-engineered devices to achieve permanent vascularization. This strategy has worked well for many tissues. However, it falls short for thick, complex tissues such as large vital organs, including liver, kidney, and heart.

In parallel to recent tissue engineering advances, the rapidly emerging field of MicroElectroMechanical Systems (MEMS) has penetrated a wide array of applications, in areas as diverse as automotives, inertial guidance and navigation, microoptics, chemical and biological sensing, and biomedical engineering. Control of features down to the submicron level can routinely be achieved in mechanical structures.

Several groups have used these highly precise silicon arrays to control cell behavior and study gene expression and cell surface interactions (See, published PCT patent application WO 00/66036; Kaihara et al., *Tissue Eng* 6(2): 105-17 (April 2000), each incorporated herein by reference). However, classical MEMS techniques are planar in nature. Silicon micromachining technology is often referred to as the "planar technology" (Grove A S, *Physics and Technology of Semiconductor Devices*, Wiley, New York, 1967). MEMS technology has not previously been adapted to the generation of thick, three-dimensional vascularized tissues.

Accordingly, there is a need in the art for precise fabrication methods capable of forming thick, three-dimensional tissues having an intrinsic blood supply system.

SUMMARY OF THE INVENTION

The invention provides methods for translating two-dimensional microfabrication technology into the third dimension, to make multilayer devices. The invention extends existing MEMS techniques for the purpose of producing two-dimensional scaffolds for organ fabrication.

A two-dimensional (x, y) mold is fabricated using high-resolution molding processes, such as micromachined wafer technology, thick photoresist processes, or other techniques, to create a patterned of "micromachined", small dimensioned channels, such that the micromachined channels are connected for the circulation of fluid in the multilayer device. From this mold, a first scaffold may be cast, resulting in a first scaffold with horizontal (x, y) pattern matching the pattern of the mold. The scaffold can be made of a biocompatible material, which can be, in several embodiments, biodegradable, partially biodegradable or non-biodegradable. This first scaffold can be joined to a second scaffold, typically of the same material. The second scaffold can be a flat, unpatterned piece, or can be a patterned piece with the same geometry as the first scaffold. When two patterned pieces with the same geometry are used, the pieces are preferably aligned, so that the micromachined channels patterned on the first scaffold are aligned with matching micromachined channels patterned on the second scaffold, to make a vasculature. In one embodiment, the vasculature has branched channels, beginning from one or more inlets, expanding into more channels, and then converging back into one or more outlets. Both scaffolds can be made of a material that is suitable for attachment and culturing of cells.

The two scaffolds can be joined or fastened by one of several techniques. In one technique, the scaffolds are stacked or tiled, one on top of the other. In another technique, a long strip or roll of scaffold material is produced from the mold and is then folded. Vessels can be formed in the third (z) dimension by forming through-holes in the scaffolds, then lining up the through-holes. The scaffolds can be aligned visually or mechanically.

A set of cells can be added to or seeded into the joined or fastened scaffolds, so that the three-dimensional scaffolds can be a template for cell adhesion and growth by the added or seeded cells. In one embodiment, the added or seeded cells can be parenchymal cells, such as hepatocytes. The set of cells can be added to or seeded onto the three-dimensional scaffolds through vessels in the joined or fastened scaffolds. A second set of cells can be added to or seeded onto the assembled scaffold system through other vessels than those used to seed the first set of cells. In one embodiment, the second set of added or seeded cells can be endothelial cells. The second set of seeded cells can thus form small-dimensioned blood vessels between and through the first set of seeded cells. Thus, in addition to serving as a mechanical framework for the organ, the assembled scaffold system provides a template for all of the microstructural complexity of the organ, so that cells have a mechanical map to locate themselves and form subsystems, such as blood vessels in the liver.

This invention can be used as a source of replacement organs for implantation into recipients with damaged or failing organs, as biodegradable scaffolds for tissue engineering, biodegradable or biocompatible life assist and bio-hybrid artificial organs and tissues, as drug delivery devices, assay systems and test devices for modeling cell attachment, or as cell-based sensors.

DETAILED DESCRIPTION OF THE INVENTION

Figure 1:
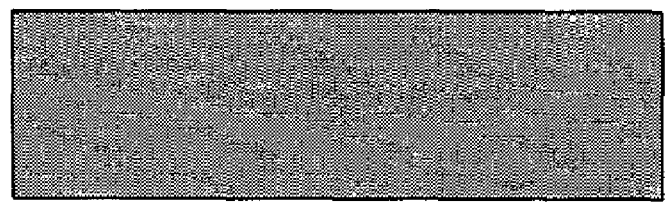
FIG. 1 is a schematic side drawing showing a single depth microfabrication process for making a mold. Here the schematic is generalized, so that the mold can be any material, including silicon, glass or polymeric materials.
Figure 1:
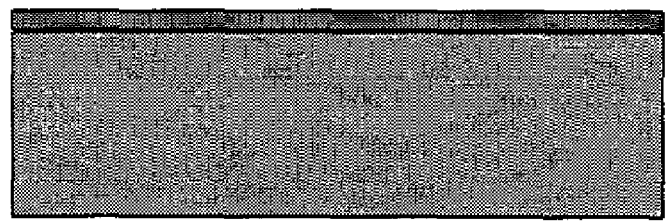
Figure 1:
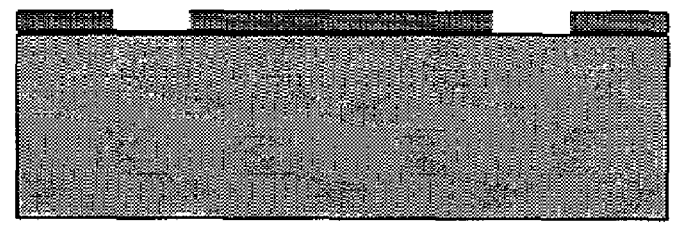
Figure 1:

General Purpose of the Invention. The invention provides a new approach for fabricating three-dimensional vascularized tissues for transplantation in human recipients in need of vital organs and other tissues with a blood supply. The invention also provides methods for translating the two-dimensional microfabrication technology into the third dimension. The invention provides for the construction of channels in thick polymer layers, enabling fabrication of an entire organ that meets requirements for oxygen transport, nutrient and metabolite movement. Thus, the invention provides low-cost, scalable techniques for producing organs large enough to transplant into animal recipients, typically vertebrate recipients, and preferably human recipients. Advantages of this invention over other methods of tissue engineering include (a) the capability for producing all of the high resolution three-dimensional structures required for complex tissues and vital organs, and (b) the ability of the mechanical (possibly biodegradable) scaffold to provide guidance for cell growth and tissue formation, rather than reliance upon biochemical factors alone.

A limitation of the prior art methods of tissue engineering is related to mass transport. Tissue engineered constructs without a blood supply leads to hypoxia and nutrient deprivation. Without vasculature, cells in constructs larger than 1-2 mm experience significant cell death. Prior art efforts to prevascularize constructs and attempts to promote vessel in-growth have both met with limited success. See, Eiselt P et al., *Biotechnol. Prog.* 14,134-140 (1998). By contrast, the tissue engineering methods of this invention produce thick, vascularized structures with preexisting vasculature.

In one embodiment, a two-dimensional (x, y) mold is fabricated using molding processes such as micromachined wafer technology, thick photoresist processes, hot embossing (Becker H & Heim U, *Silicon as Tool Material for Polymer Hot Embossing*, 12th IEEE International Conference on MEMS, eds. Najafi K & Gabriel K, 228 (1999)), micromachined structural polymers (Pan L-W et al., *Cylindrical Plastic Lens Array Fabricated by a Micro Intrusion Process*, 12th IEEE International Conference on MEMS, eds., Najafi K & Gabriel K, 217 (1999)), reconfigurable materials (Armani D et al., *Re-Configurable Fluid Circuits by PDMS Elastomer Micromachining*, 12th IEEE International Conference on MEMS, eds., Najafi K & Gabriel K, 222 (1999)) or other techniques. From this original mold, a scaffold is cast in a biocompatible, biodegradable material. This scaffold is joined to second scaffold of the same material; the additional scaffold may be a flat, unpatterned piece, or may be a patterned piece with the same geometry as the first scaffold. Once the two scaffolds are joined, this method of the invention begins building into the third (z) dimension.

The three-dimensional scaffold can be a biodegradable scaffold. Biodegradable scaffolds serve as the template for cell adhesion and growth, as the tissue-engineered organ takes form over the skeleton of the scaffold. The cells that grow on the multicellular device of the invention are animal cells, typically vertebrate cells. In addition to serving as a mechanical framework for the organ, the scaffold, ideally, provides a template for all of the microstructural complexity of the organ, so that cells have a mechanical roadmap to locate themselves and form subsystems such as blood vessels and bile ducts in the liver. Once the organ has formed over the scaffold, the inlet and outlet blood vessels are sewn into the organ recipient, and the polymer scaffold biodegrades harmlessly.

This invention provides sufficient fabrication resolution to provide templates for the small-diameter blood vessels (capillaries) or other vasculature that predominate an organ. By contrast, prior art three-dimensional printing technologies that use polymers suitable for biodegradable tissue engineering have a minimum resolution of roughly 300 microns, about 40 times larger than what is required for the small capillaries. The invention differs from methods such as solid free-form fabrication (see, U.S. Pat. Nos. 6,139,574 and 6,176,874, incorporated herein by reference), because the invention produces a template or scaffold with a resolution two orders of magnitude better than solid free-form fabrication techniques. The invention also differs from other MEMS technology, because the invention translates two-dimensional (x, y) fabrication technology into the third (z) dimension, making complex organ fabrication possible. This invention is thus an improvement of other technologies, which were able to produce two-dimensional sheets of tissue. See, published PCT patent application WO 00/66036; Kaihara et al., *Tissue Eng* 6(2): 105-17 (April 2000).

By extending this technology in any of the three dimensions as needed, one of skill in the art can move from the presently achievable formation of small 70 $cm^2$ sheets, each containing one plane of blood vessels, of polymeric scaffold, to the formation of perhaps 25 $cm^3$ of material, enough to build an organ. Thus, the invention advantageously provides a new capability for producing the high resolution three-dimensional structures required for complex tissues and vital organs, and the ability of the mechanical scaffold to provide guidance for cell growth and tissue formation rather than reliance upon biochemical factors alone. The process can be customized for the physiology of a particular patient.

Micromachined Wafer Technology; Mold and Scaffold Fabrication. Fabrication of the molds begins by selection of an appropriate substrate for the micromachining process. The choice of a substrate material for the mold is guided by many considerations, including the requirements placed on the fabrication process by the desired mold dimensions, the desired size of the ultimate template, the surface properties of the wafer, and the interaction of the wafers with the various cell types, extracellular matrix molecules ("ECM"), and any polymeric backbone. Cost may also be a consideration.

Then, the process sequence for mold generation is defined. The geometry of the mold, in particular the number of different feature depths required, is the major factor determining the specific process sequence.

Silicon. Typically, micromachining is performed on standard bulk single crystal silicon wafers of a diameter ranging between 50 and 300 millimeters, and of thickness ranging between 200 and 1200 microns. These wafers can be obtained from a large number of vendors of standard semiconductor material, and are sawn and polished to provide precise dimensions, uniform crystallographic orientation, and highly polished, optically flat surfaces.

Additional guidance to micromachining in silicon is provided in EXAMPLE 1. The micromachining in silicon can be observed by the use of epifluorescence microscopy or by the use of metallurgic microscope. Alternatively, the micromachining can be observed by an electron microscope, such as an environmental scanning electron microscope (ESEM).

Glass. Wafers made from Pyrex®, other borosilicate glass, or other glasses can also be procured and inserted into micromachining processes, with alternative processes used to etch the glassy materials. See, published PCT patent application WO 00/66036; Kaihara et al., *Tissue Eng* 6(2): 105-17 (April 2000). Pyrex®, a standard borosilicate glass available from Corning, is another important material for the development of tissue engineered structures. Pyrex® differs from silicon in several important ways, including its transparency, a natural tendency toward hydrophilicity, the availability of a range of alternate wet chemical etch techniques, and a lower potential long-term cost for material. An important difference relates to the cost; silicon is expensive because of the extraordinary measures taken to purify the material from part-per-billion transition metal contaminants. Such purification methods are used because of the requirements of the integrated circuit manufacturing process, and are not synonymous with the needs of the biomedical industry. The cost of silicon rises dramatically as wafer size is increased, because of the complexity involved in growing, purifying and slicing larger wafers (Wolf S & Tauber R N, *Silicon Processing for the VLSI Era* (Lattice Press, Sunset Beach, Calif., 1986)). By contrast, very large sheets of Pyrex® can be produced and processed at relatively low cost.

We have microfabricated Pyrex® templates using two different wet chemical etch processes, one involving hydrofluoric/nitric acid mixtures, and the other involving hydrofluoric and phosphoric acid mixtures. Each of these mixtures requires a hard etch mask; a material which can be lithographically patterned with high fidelity and does not suffer significant erosion or adhesion loss during subsequent etching. The standard etch mask employed for these experiments is a layer of polysilicon, deposited by a Low Pressure Chemical Vapor Deposition (LPCVD) process. Polysilicon deposition occurs between 550 and 650° C. in an evacuated process tube; these high temperatures cause the glass to flow and buckle, leading to severe downstream processing problems.

Additional guidance to micromachining in glass is provided in EXAMPLE 2. The micromachining in glass can be observed by the use of transmission microscope. Alternatively, the micromachining can be observed by an electron microscope, such as an environmental scanning electron microscope (ESEM).

Polymeric Materials. The use of polymeric materials has also begun recently; special etching technologies have been developed which are capable of producing ultrafine dimensions in these materials as well. We have performed the direct machining of polymeric materials and have developed special etching technologies that are capable of producing ultrafine dimensions in polymeric materials (see, EXAMPLES 3 and 4). Other methods for direct micromachining of polymeric materials are known in the art, for example, U.S. Pat. No. 6,136,212.

Many polymeric materials can be used to create the mold or scaffold of the invention. Among the materials that can be used to create the scaffolds are polymers made of representative synthetic polymer blocks, including polyphosphazenes, poly(vinyl alcohols), polyamides, polyester amides, poly(amino acid)s, synthetic poly(amino acids), polyanhydrides (such as polyanhydride co-polymers of fumaric and sebacic acid (poly(FA:SA)), polycarbonates (U.S. Pat. Nos. 5,099,060 and 5,198,507), polyarylates (U.S. Pat. No. 5,216,115), polyacrylates, polyalkylenes, polyacrylamides, polyalkylene glycols, polyalkylene oxides, polyalkylene terephthalates, polyortho esters, polyvinyl ethers, polyvinyl esters, polyvinyl halides, polyvinylpyrrolidone, polyesters, polylactides, polyglycolides, polysiloxanes, polyurethanes and copolymers thereof. See, U.S. Pat. No. 6,160,084; or *The Polymer Handbook*, 3rd edition (Wiley, N.Y., 1989). The utility of a polymer as a tissue engineering substrate is primarily dependent upon whether it can be readily fabricated into a three-dimensional scaffold.

Examples of suitable polyacrylates include poly(methyl methacrylate) (PMMA), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate). Other examples of suitable polymers include the polyethylene oxide/polyethylene terephthalate disclosed by Reed et al., *Trans. Am. Soc. Artif. Intern. Organs*, 109 (1977); bisphenol-A based polyphosphoesters, including poly(bisphenol-A phenylphosphate), poly(bisphenol-A ethylphosphate), poly(bisphenol-A ethylphosphonate), poly(bisphenol-A phenylphosphonate), poly[bis(2-ethoxy)hydrophosphonic terephthalate], and copolymers of bisphenol-A based poly(phosphoesters) (see, U.S. Pat. No. 5,686,091); and polymers of tyrosine-derived diphenol compounds. Methods for preparing the tyrosine-derived diphenol monomers are disclosed in U.S. Pat. Nos. 5,587,507 and 5,670,602.

The polymer should be selected for biocompatibility at the time of implant, Any degradation products should also be biocompatible. Relatively high rigidity is advantageous so that the scaffold can withstand the contractile forces exerted by cells growing within the scaffold. Also important are the thermal properties, especially the glass transition temperature (Tg) which must be high enough so that the network of pores in the scaffold does not collapse upon solvent removal.

A biocompatible degradable polymer and its degradation products are non-toxic toward the recipient. The term "biodegradable" refers to materials that are bioresorbable and/or degrade and/or break down by mechanical degradation upon interaction with a physiological environment into components that are metabolizable or excretable, over a period of time from minutes to three years, preferably less than one year, while maintaining the requisite structural integrity. As used in reference to polymers, the term "degrade" refer to cleavage of the polymer chain, such that the molecular weight stays approximately constant at the oligomer level and particles of polymer remain following degradation. The term "completely degrade" refers to cleavage of the polymer at the molecular level such that there is essentially complete mass loss. The term "degrade" as used herein includes "completely degrade" unless otherwise indicated. PLGA, as well as PLA and PGA have been used to make biodegradable implants drug delivery. See, U.S. Pat. No. 6,183,781 and references cited therein. Biodegradable materials have been developed for use as implantable prostheses, as pastes, and as templates around which the body can regenerate various types of tissue. Polymers that are both biocompatible and resorbable in vivo are known in the art as alternatives to autogenic or allogenic substitutes.

Representative synthetic biodegradable polymer segments or polymers include polyhydroxy acids, such as polylactides (PLA), polyglycolides (PGA), and copolymers thereof; poly(ethylene terephthalate); poly(hydroxybutyric acid); poly(hydroxyvaleric acid); poly[lactide-co-($\epsilon$-caprolactone)]; poly[glycolide-co-($\epsilon$-caprolactone)]; polycarbonates, poly(pseudo amino acids); poly(amino acids); poly (hydroxyalkanoate)s; polyanhydrides; polyortho esters; and blends and copolymers thereof. These bioerodable polymers also include polyacetals, polycyanoacrylates, poly(ether ester)s, poly(dioxanone)s, poly(alkylene alkylate)s, copolymers of poly(ethylene glycol) and poly(ortho ester), degradable polyurethanes and copolymers and blends thereof. Also included are non-bioerodable polymers such as polyacrylates, ethylene-vinyl acetate copolymers, acyl-substituted cellulose acetates, non-degradable polyurethanes, polystyrenes, polyvinyl chloride, polyvinyl fluoride, poly(vinylimidazole), chlorosulfonate polyolefins, and polyethylene oxide. Any suitable blends or copolymers of these materials can also be used. Solvent/nonsolvent systems suitable for a given polymer can be determined via routine experimentation. See, U.S. Pat. No. 6,183,781.

Rapidly bioerodible polymers such as polylactide-coglycolides, polyanhydrides, and polyorthoesters, which have carboxylic groups exposed on the external surface as the smooth surface of the polymer erodes, can also be used. In addition, polymers containing labile bonds, such as polyanhydrides and polyesters, are well known for their hydrolytic reactivity. Their hydrolytic degradation rates can generally be altered by simple changes in the polymer backbone and their sequence structure.

Particularly useful for this invention are polyesters in the polylactide(PLA)/polyglycolide(PLG) family. These polymers have received a great deal of attention in the drug delivery and tissue regeneration areas. They have been in use for over 20 years in surgical sutures, are Food and Drug Administration (FDA)-approved and have a long and favorable clinical record. A wide range of physical properties and degradation times can be achieved by varying the monomer ratios in lactide/glycolide copolymers. Poly-L-lactic acid (PLLA) and poly-glycolic acid (PGA) exhibit a high degree of crystallinity and degrade relatively slowly, while copolymers of PLLA and PGA, PLGAs, are amorphous and rapidly degraded.

A preferred polymeric material that can be used to create the scaffolds is poly(D,L-lactide-co-glycolide (polylactide-co-glycolide; PLGA). PLGA is biocompatible and biodegradable. Particularly useful for the practice of the invention, PLGA can be stacked or bonded. PLGA can also be of varying and controllable porosity. Moreover, PLGA can be cast, stamped, or embossed. Direct etching of PLGA is also possible. Using the micromachining methods of the invention, one can obtain roughly the same level of detail from polymeric materials as from photolithography of silicon (compare, published PCT patent application WO 00/66036; Kaihara et al., *Tissue Eng* 6(2): 105-17 (April 2000)). In general, the detail that can be obtained in the polymeric material is as good as the mold.

Methods for making biodegradable polymers in desired shapes are known in the art. See, U.S. Pat. No. 6,165,486. Suitable solvents for forming the polymer solution include methylene chloride, acetone, ethyl acetate, methyl acetate, tetrahydrofuran and chloroform. For example, a solution D,L-PLGA can readily be prepared in methylene chloride. Solvent casting is one of the most widely used processes for fabricating scaffolds of degradable polymers. See, U.S. Pat. Nos. 6,103,255; 5,686,091; 5,723,508; 5,514,378; Mikos et al., *Polymer* 35: 1068-77, (1994); de Groot et al., *Colloid Polym. Sci.* 268: 1073-81 (1991); and Laurencin et al., *J. Biomed. Mater. Res.* 30: 133-8 (1996)).

The mechanical compression of a polymer can be accomplished in one of several ways. For example, a desired amount of polymer matrix can be weighed out and compressed with a mechanical press. The resulting wafer can be implanted whole, or cut into smaller pieces to be implanted individually. A general procedure for preparing biodegradable polymer blends using the cold-pressing technique involves taking polymer scaffolds that have been prepared using the solvent-casting technique, prior to leaching the NaCl, cutting them into discs of a diameter of 1.2 cm, and pressing at a pressure of 10,000 psi using a Carver hydraulic press. The 1 mm thick discs are then immersed in distilled water to dissolve the NaCl (see, U.S. Pat. No. 6,165,486). A general procedure for preparing biodegradable polymer blends using the hot-pressing technique involves placement of cold-pressed polymer scaffolds in an oven at 130° C. for 15 minutes. The hot die containing the cold-pressed scaffold is pressed again at 10,000 psi using a Carver hydraulic press, cooled to room temperature, removed, and immersed in distilled water to dissolve the NaCl (see, U.S. Pat. No. 6,165,486).

The method of forming or sealing the polymers can include heating the polymer, for example, heating the polymer transiently to at least the glass transition temperature of the polymer. This can be done to optimize the characteristics, such as resilience or surface morphology, of the final product.

Biodegradable polymers can also be constructed with various porosities. Biodegradable porous scaffolds are characterized by a substantially continuous polymer phase, having a highly interconnected bimodal distribution of open pore sizes with rounded large pores of about 50 to about 500 microns in diameter and rounded small pores less than 20 microns in diameter. Biodegradable polymers typically have average molecular weights of greater than 2000 daltons and often as high as 50,000 to 250,000 daltons. Methods of preparing polymeric tissue scaffolds are disclosed in U.S. Pat. No. 6,103,255.

Biocompatible, non-biodegradable polymers can also be used in the invention for constructing artificial organs where the scaffold is not intended to degrade following implantation. Examples of non-biodegradable polymer segments or polymers include ethylene vinyl acetate, poly(meth)acrylic acid, polyamides, polyethylene, polypropylene, polystyrene, polyvinyl chloride, polyvinylphenol, and copolymers and mixtures thereof.

A preferred non-biodegradable polymeric material that can be used to create the scaffolds is polydimethylsiloxane (PDMS). Silicones are polymeric organosilicon compounds. The repeating $(SiO(CH_3)_2)$ unit is the monomer of which the polymer PDMS is composed. There are six classes of silicone products: fluids, lubricants, elastomers (rubbers), resins, emulsions, compounds and fluids. Each of these classes depends upon the number of the monomeric units and the degree to which the chains are crosslinked. Elastomers are used for the polymeric scaffold material in this invention.

PDMS is a common structural material used in biomedical applications (Hong J W, *IEEE-EMBS Conf. Microtechnol*. In *Medicine* and *Biology*, 407 (2000)). We have use several recent developments in the PDMS processing, including the formation of PDMS templates from SU-8 patterns, and the bonding of PDMS layers together to form closed chambers with fully sealed lumens. Measurements of the PDMS layers using interferometric characterization indicate that 5 micron to more than a millimeter thicknesses may be routinely obtained. A WYKO® interferometer image (Borenstein J et al., *Micromachining and Microfabrication Process Technology II*, Eds. Pang SW and Chang S-C, *SPIE* 2879, 116 (1996)), indicates a depth of 50 microns for channels molded into a PDMS layer from a SU-8 master.

Like PLGA, PDMS can be stacked or bonded; can be made of varying and controllable porosity; and can be cast, stamped, or embossed. Using the micromachining methods of the invention, one can obtain roughly the same level of detail from polymeric materials as from photolithography of silicon.

Another non-biodegradable polymeric material that can be used to create the scaffolds is polymethylmethacrylate (PMMA).

Moreover, advances in polymer chemistry can aid in the mechanical tasks of lifting and folding as well as the biologic tasks of adhesion and gene expression.

The polymeric material of the layers of the multilayer device of the invention can be a unique temperature-responsive polymer, poly-N-isopropyl acrylamide (PNIPAAm), which demonstrates a fully expanded chain conformation below 32° C. and a collapsed, compact conformation at high temperatures. When grafted onto surfaces of silicon wafers using electron beam irradiation, it can be used as a temperature switch for creating hydrophilic surfaces below 32° C. and a hydrophobic surfaces above 32° C. Since PNIPAAm is insoluble in water over the lower critical solution temperature (LCST about 32° C.) and reversibly solubilized below the LCST, cells detach from the substratum by simply lowering the temperature below the LCST. One of skill in the art can (1) engraft the polymer on silicon wafers that are pre-coated with polystyrene or (2) engraft the polymer on silicon wafers whose surface is first modified by vinyl-tricholorosilane. Either of these techniques will ensure that the polymer is better integrated and conjugated to its substratum (polystyrene in the former case and vinyl groups in the later case) so that it can serve as an effective thermal switch, useful in reversing cell attachment and detachment as a single contiguous layer of cells without the usual cell damage.

Another polymer system can involve the use of RGD (Arg-Gly-Asp) peptides. The RGD sequence is part of the domain within the fibronectin molecule that endows it with the ability to interact with the cell surface of fibroblasts. Fibronectin itself is a well-characterized extracellular, structural glycoprotein which interacts strongly with other extracellular matrix molecules and which causes the attachment and spreading of most cells. This function of the fibronectin molecule is localized primarily to the RGD sequence. One of skill in the art can synthesize RGD peptides with a structural backbone of PMMA with an RGD peptide sequence at its tips, both bound to one another with the intermediate layering of PEO. This allows differential cell adhesion in only selected areas and not others. Once the tissue of desired quality is formed, release of this intact monolayer of tissue from its substratum is straightforward; it requires only the addition of soluble RGD to the culture medium to act as a competitive substrate to the insolubilized RGD comb substrate on the silicon surface.

Another polymer system that can be used is poly(lactic-co-glycolic acid) (PLGA) and poly-4-hydroxybutarate (P4HB). Both polymers are biocompatible, and exhibit a wide range of erosion times and mechanical properties. Thus, they have been very attractive candidates for tissue engineering. We have made films of PLGA and P4HB that accurately replicate the etched surfaces of the silicon. This system can be used to eliminate the lifting problem; it would allow one of skill in the art to culture endothelial cells within the branched networks of the polymer and hepatocytes or other cell types on the top and bottom outer polymer surfaces.

Silicon Mold Fabrication. The simplest method for creating a device of the invention, beginning with a single depth dimensions for the mold, is shown in FIG. 1. The schematic is generalized so that processing of silicon, glass or polymeric materials are covered. Specifically, for a silicon substrate, the process sequence is as follows.

First, the silicon wafer is cleaned, and a layer of photosensitive material is applied to the surface. Typically, the layer is spun on at a high revolution rate to obtain a coating of uniform thickness. The photoresist is baked, and the wafer is then exposed to ultraviolet or other short-wavelength light through a semi-transparent mask. This step can be accomplished using any one of several masking techniques, depending on the desired image resolution.

Then, the resist is then developed in appropriate developer chemistry, and the wafer is then hard-baked to remove excess solvent from the resist. If the lithographic process produces a thick enough layer, the photosensitive layer itself can be used as the mold for polymer casting and subsequent fabrication. If not, once the lithographic process has been completed, the wafer can be etched in a plasma reactor using one of several possible chemistries. Etching serves to transfer the two-dimensional pattern (x, y) into the third dimension, a specified depth into the wafer. Plasma parameters are determined by the desired shape of the resulting trench (semi-circular, straight-walled profile, angled sidewall, etc.) as well as by the selectivity of the etchant for silicon over the masking photoresist. When the etching has been completed, the photoresist can be removed and the wafer prepared for use in the tissue molding process.

Figure 2:
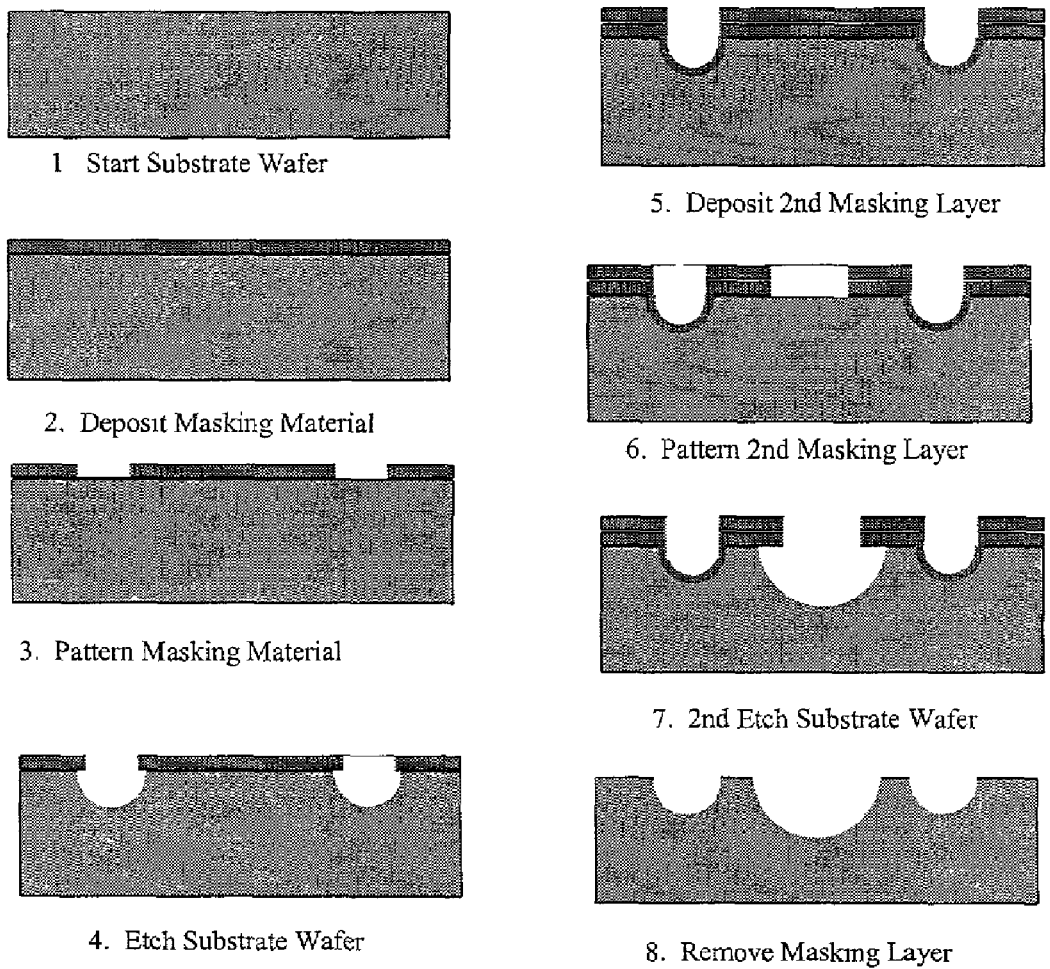
FIG. 2 is a schematic side drawing showing a multi-depth microfabrication process.

For a more advanced fabrication, a multi-depth microfabrication process can be used, such as is shown in FIG. 2.

Figure 3:
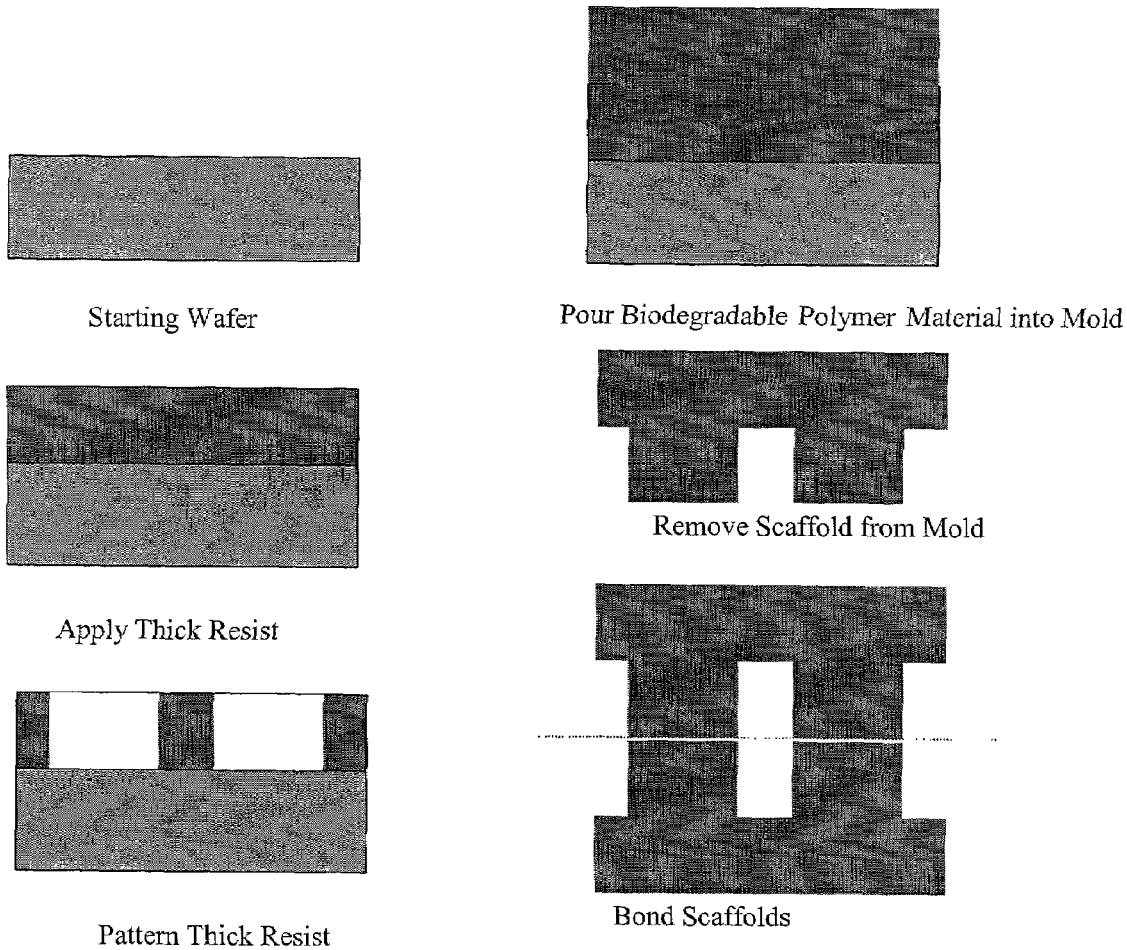
FIG. 3 is a schematic side drawing showing a polymeric scaffold fabrication using the microfabricated mold.

Scaffold Fabrication. A scaffold fabrication process is described in FIG. 3. A mold is formed either by using micromachining of silicon, glass, ceramics or other wafer materials or by forming a mold using electroforming, thick photoresist processing, or other mold production techniques. Once the mold has been formed, suitable polymer material is poured into the mold, and the cast removed. This cast, or scaffold, now has the pattern of channels desired to form the vascular pattern. Scaffolds may then be joined to form lumens, or closed vessels, upon which cells may be seeded and tissue formed. Subsequent molds may be produced either by repeating the micromachining process described above, or by utilizing the polymer casts as molds for additional polymer films fabricated using other polymer materials.

The material of choice for the scaffold network is preferably a polymer, but the scaffold can be made of other materials, including glasses, silicon, metals and ceramics. Polymer materials may be biocompatible, biodegradable, or involve combinations of both. Surfaces may be treated chemically or may be coated with proteins or other chemical or biological species as required by the specific application. Materials may be porous, non-porous, or may involve combinations of porous and non-porous films.

After the mold has been formed, a suitable polymer material is poured into the mold, the polymer cast solidifies, and the cast is removed. This cast, or scaffold, now has the desired pattern of channels to form the vascular pattern.

The channels have a branched pattern, with the smallest channels having a dimension of from about 5 microns to about 500 microns (see below and EXAMPLE 1).

Figure 4:
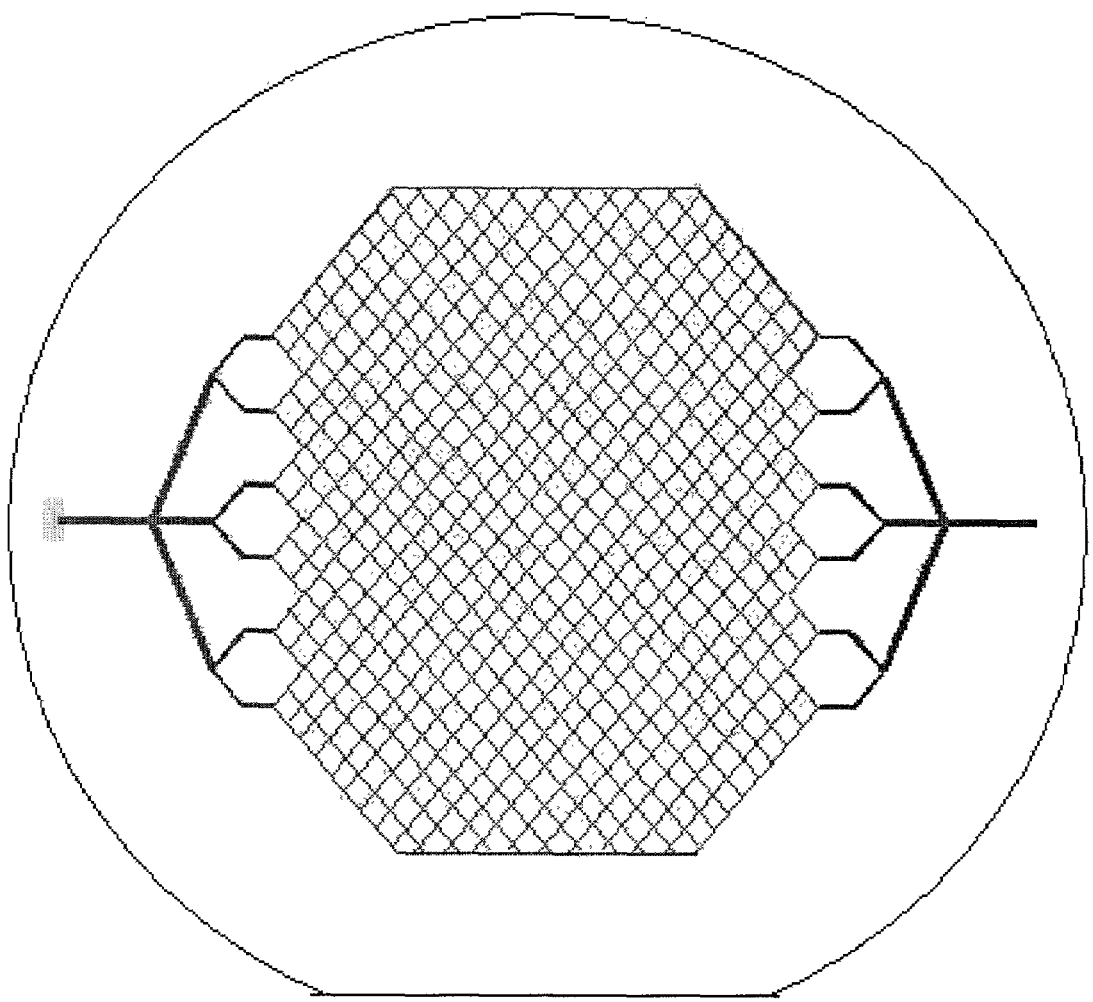
FIG. 4 is a schematic of vascular pattern used to produce TEP-0 wafers.
Figure 5:
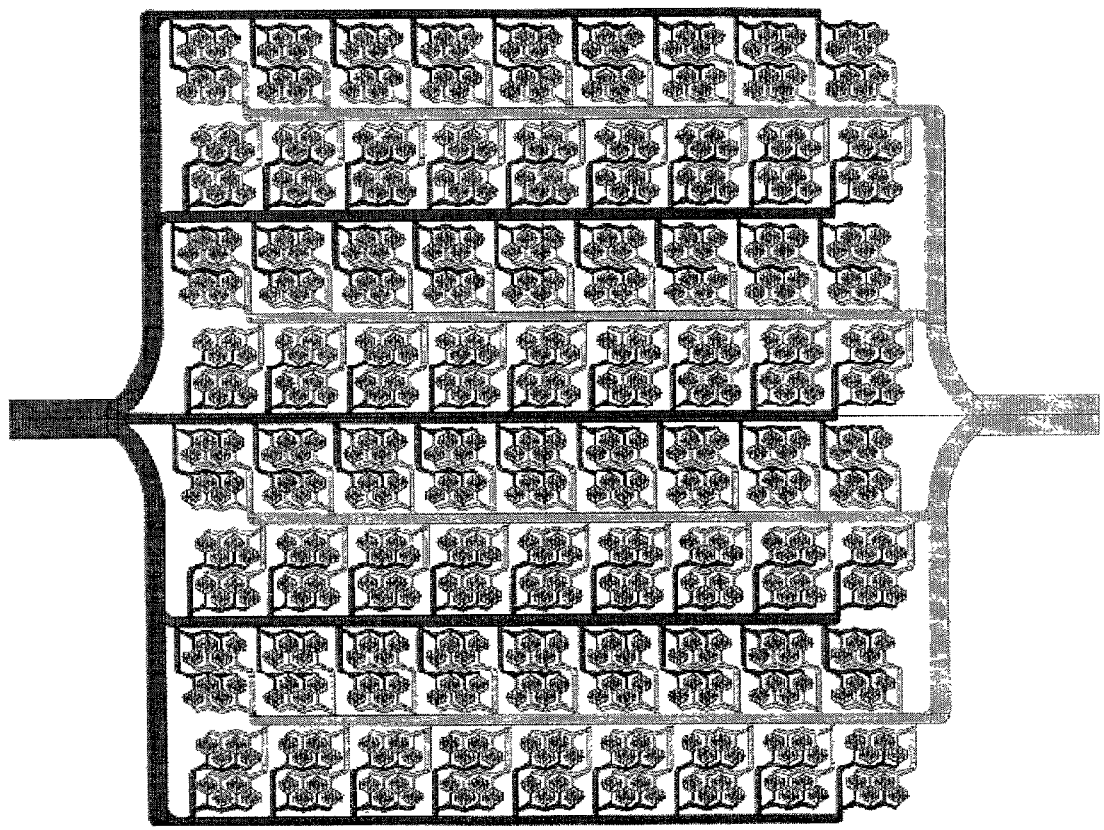
FIG. 5 is a schematic of vascular pattern used to produce TEP-1 wafers. The interdigitated structure has improved fluid flow properties as compared to TEP-0.
Figure 6:
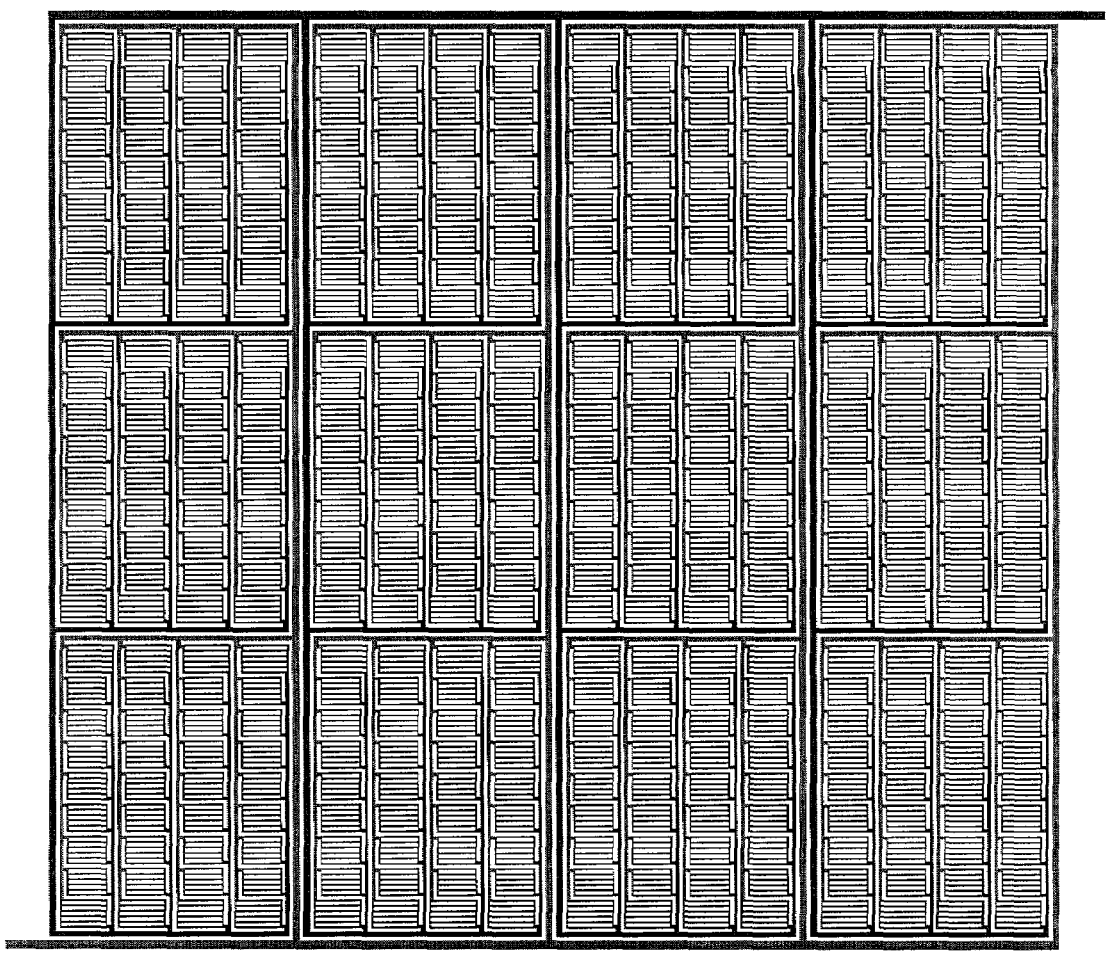
FIG. 6 is a schematic of vascular pattern used to produce TEP-2a wafers.

Among the vascular patterns are several vascular networks have been produced using a series of evolutionary fluid dynamic designs. The first of these, TEP-0 (see, FIG. 4), was based upon the twin goals of concentrating more than 85% of the vascular cross section within the capillaries, and providing a stepwise scaling from arteries and veins down to capillaries. Cell seeding and lifting was successfully demonstrated with TEP-0, but flow rates were much lower than physiological goals, with concomitantly higher pressure drops. A second design, TEP-1 (see, FIG. 5), provided high capillary cross section but increased the flow rate and reduced the pressure drop substantially, as is shown in TABLE 1, below. A third design, TEP-2a (see, FIG. 6), further increased the flow rates, and is specifically designed to provide uniform flow throughout. Each of these prototypes was designed using simple fluid resistance circuit analysis, a valid first approximation but with significant limitations for full implementation.

The capillaries in the TEP-2a are longer, so if all the capillaries from each wafer were laid end-to-end, the TEP-1 would make a 6-meter long capillary and the TEP-2a would make an 11-meter long capillary. Also, at normal liver conditions (pressure drop of about 9 mmHg from inlet to outlet), 3 µl of blood can flow through the TEP-1 each minute, compared to 170 µl/min for the TEP-2a. Other differences include that the TEP-2a has thinner capillaries (20 microns×35 microns rather than 30 microns×40 microns for the TEP-1) and that all capillaries in the TEP-2a have the same flow rate and fluid velocity, while on the TEP-2 there are some that have no flow and others that have backwards flow.

TABLE 1

Dimensional data and total flow-through measurements for several prototypes

| | No. Capillaries | Cap. Dimension | Flow @ 9 mm Hg |
|---|---|---|---|
| TEP-0 | 1,000,000 | 35 × 20 µm$^2$ | 0.004 µl/min |
| TEP-1 | 46,080 | 30 × 40 µm$^2$ | 3 µl/min |
| TEP-2a | 31,416 | 25 × 35 µm$^2$ | 170 µl/min |
| Testnet0 | 280 | 30 × 35 µm$^2$ | 26 µl/min |

TABLE 1-continued

Dimensional data and total flow-through measurements for several prototypes

|  | No. Capillaries | Cap. Dimension | Flow @ 9 mm Hg |
| --- | --- | --- | --- |
| Testnet1 | 2700 | 30 × 35 μm$^2$ | 7 μl/min |
| Testnet2 | 900 | 30 × 35 μm$^2$ | 2.2 μl/min |

The geometry of the microcirculation follows a fractal rather than Euclidean pattern (Kaandorp J A, *Fractal Modelling, Growth and Form in Biology* (Springer-Verlag, Berlin, 1994)). Such limitations can be overcome by utilizing mathematical models to describe channel networks, rather than by using conventional MEMS Computer-Aided Design tools. We have broadened pattern generation methods by the use of fractal networks. Such networks are approximated by irregular ramifying branching structures, with design rules to handle phenomena such as anastomosis.

For the placement of channels to provide conduits for appropriate distribution of blood flow, one of skill in the art should take into consideration (1) the available pressure drop driving force and (2) the diffusion distance. See, U.S. Pat. No. 6,176,874. One approach to creating the appropriate tissue architecture in vitro is to construct a branching system. See, published PCT patent application WO 00/66036; Kaihara et al., *Tissue Eng* 6(2): 105-17 (April 2000). Blood vessels are designed to imitate the parameters of the naturally occurring vascular structure. The diameter of the lumens is increased to compensate for the thickness of the subsequently seeded endothelial cells proliferate to cover the lumen walls. The blood vessel lumens are interconnected throughout the matrix so that one or more inlets can be anastomized to one or more arteries at the time of implantation, and one or more outlets anastomized to one or more veins. In an embodiment using biodegradable polymer (such as PLGA) to form the matrix, the matrix eventually degrades to leave only the seeded cells forming blood vessels that are virtually indistinguishable from natural blood vessels.

Plasma Etching. For the tissue engineering application, plasma etching has many distinct advantages over wet chemical etch processes. One of the most important advantages held by the plasma etching technology is the ability to control the width of etched features as the depth of the channel is increased. Wet chemical processes typically widen the trench substantially as the depth is increased, leading to a severe limitation on the packing density of features (Fruebauf J & Hannemann B, *Sensors and Actuators* 79: 55 (2000)). For vascularized tissue engineered scaffolds, capillaries should be space very closely together in order to maintain appropriate oxygen transport properties in the growing tissue. If the etched features are spaced too far apart, oxygen diffusion will be inadequate, leading to necrosis. If the etched features are spaced too closely together, features will blur together as the depth of the channels is increased. Plasma etching enables an additional level of control; not only is control of the depth of etched features excellent, but the width may be independently controlled as well.

Several different plasma etching technologies have been recently developed. One of the newest and most powerful tools is known as High Aspect Ratio Micromachining (HARMS; Ayon A A et al., *J. Vac. Sci. Tech.* 18: 1412 (2000); Hynes A M et al., *Sensors and Actuators* 74: 13 (1999)) A major advance realized by HARMS technology is the ability to etch channels of virtually unlimited depth without increasing the width of lithographically defined features. Channels etched using HARMS technology maintained their width to +/−1 micron for trenches as deep as 40 microns. This process control is obtained by maintaining sidewall angles of 90+/−1°.

Rounded Etch Profiles. Appropriate control of channel geometry can have very advantageous effects on cell seeding and on the viability of the growing tissue. Sharp angles lead to poor lining by endothelial cells, and to tearing of confluent tissue that stretches across these sharp transitions. Plasma processes typically control sidewall erosion during trench formation by trading off the level of directional sputtering with the amount of chemical etching that occurs via active species (Wolf S & Tauber RN, *Silicon Processing for the VLSI Era* (Lattice Press, Sunset Beach, Calif., 1986)). When chemically active species predominate, etching proceeds isotropically, and the width of channels increases micron-for-micron with the trench depth. The other extreme occurs when highly directional sputtering occurs, leading to very straight sidewalls and sharp corners. Analysis of the response surface for plasma etch processes demonstrates the tradeoff between isotropic and anisotropic etch behavior, presenting the opportunity for achieving an optimal point for channel widening versus the angles defined at the bottom of trenches and at corners.

Figure 7:
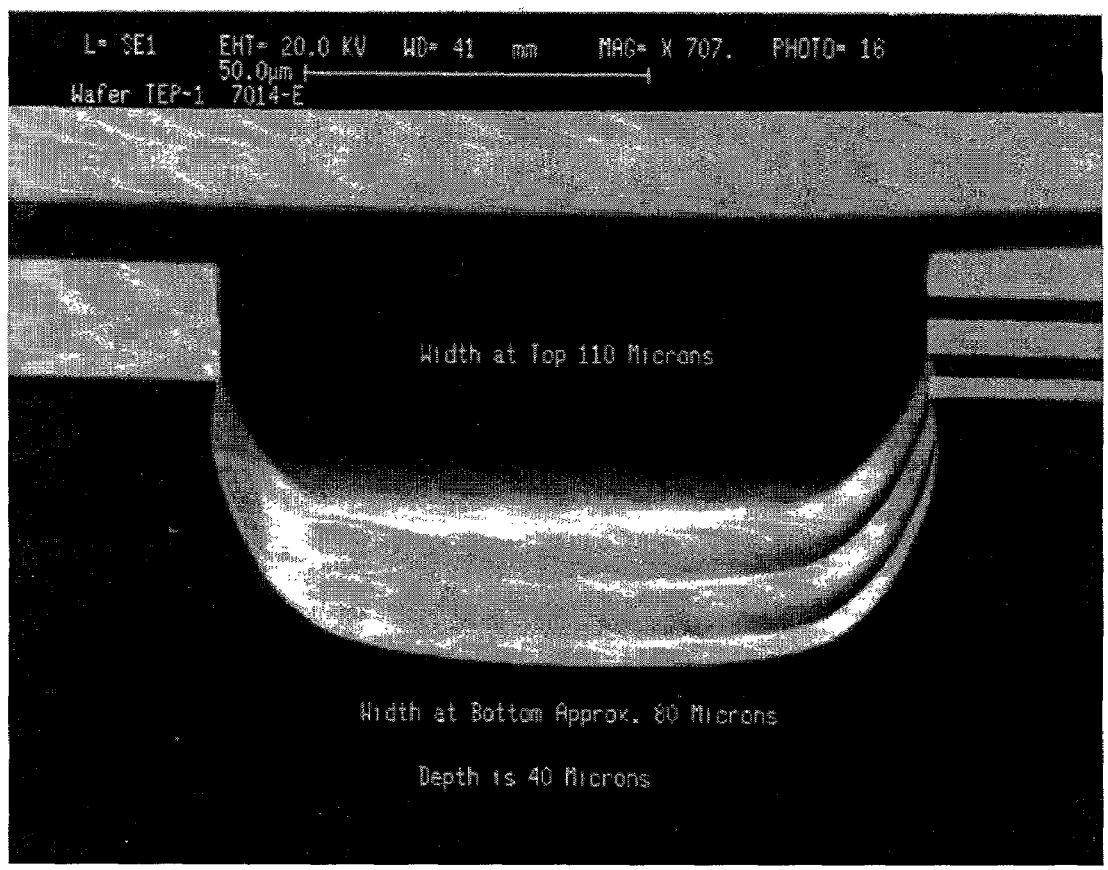
FIG. 7 is a scanning electron micrograph of a channel following optimized plasma etching, which produces high definition and rounded channels.

We have produced silicon scaffolds plasma-etched using processes that provide acceptable channel widening and near-perfect rounded corners and interfaces (FIG. 7). Cell seeding and lifting experiments have demonstrated the clear advantages of these rounded etch profiles.

Figure 8:
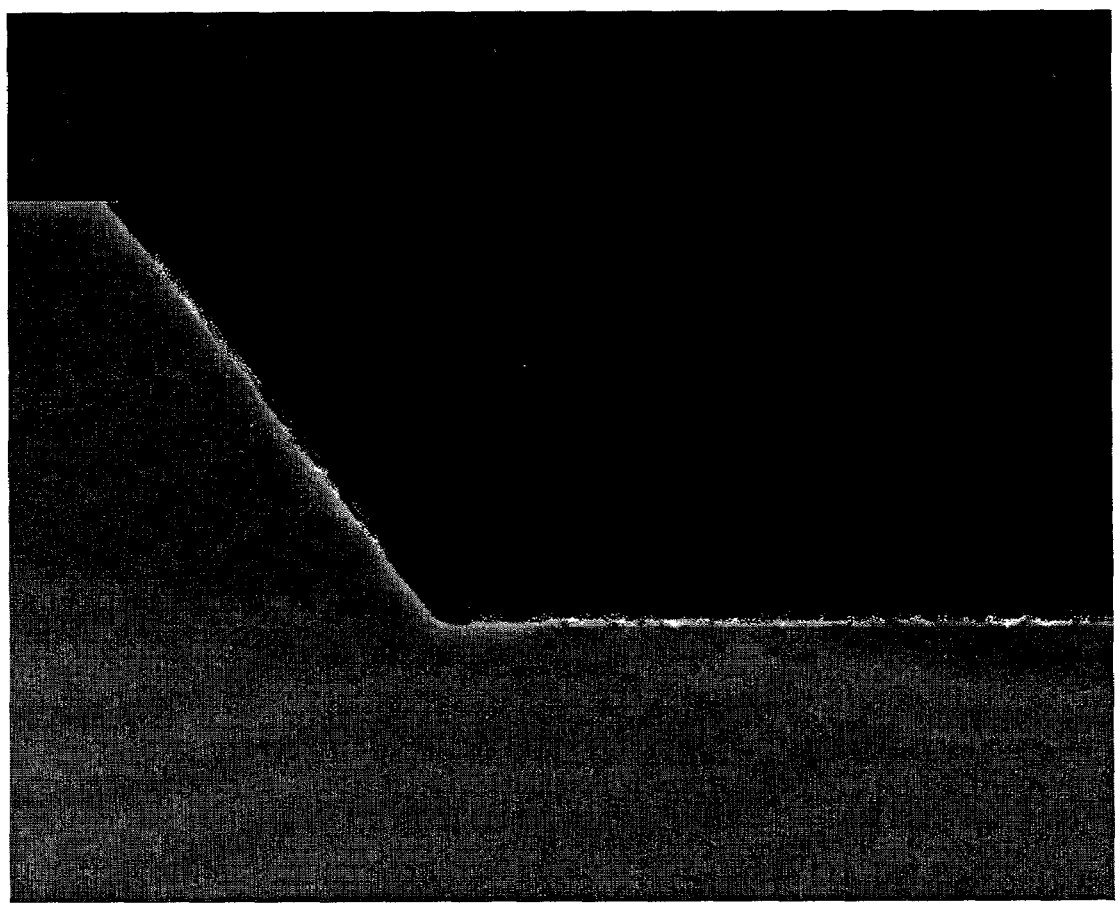
FIG. 8 is a scanning electron micrograph of an angled sidewall produced by KOH etching.

An alternative approach to obtaining with etch profiles without sharp edges is to produce angled sidewalls using anisotropic etching in KOH, such as is shown in FIG. 8 and in EXAMPLE 1.

Another approach is the use of corner compensation (Kaandorp J A, *Fractal Modelling, Growth and Form in Biology* (Springer-Verlag, Berlin, 1994)), a MEMS fabrication procedure which produces highly-controlled final etch geometries from patterns which compensate for known crystalline etching behavior.

Figure 9:
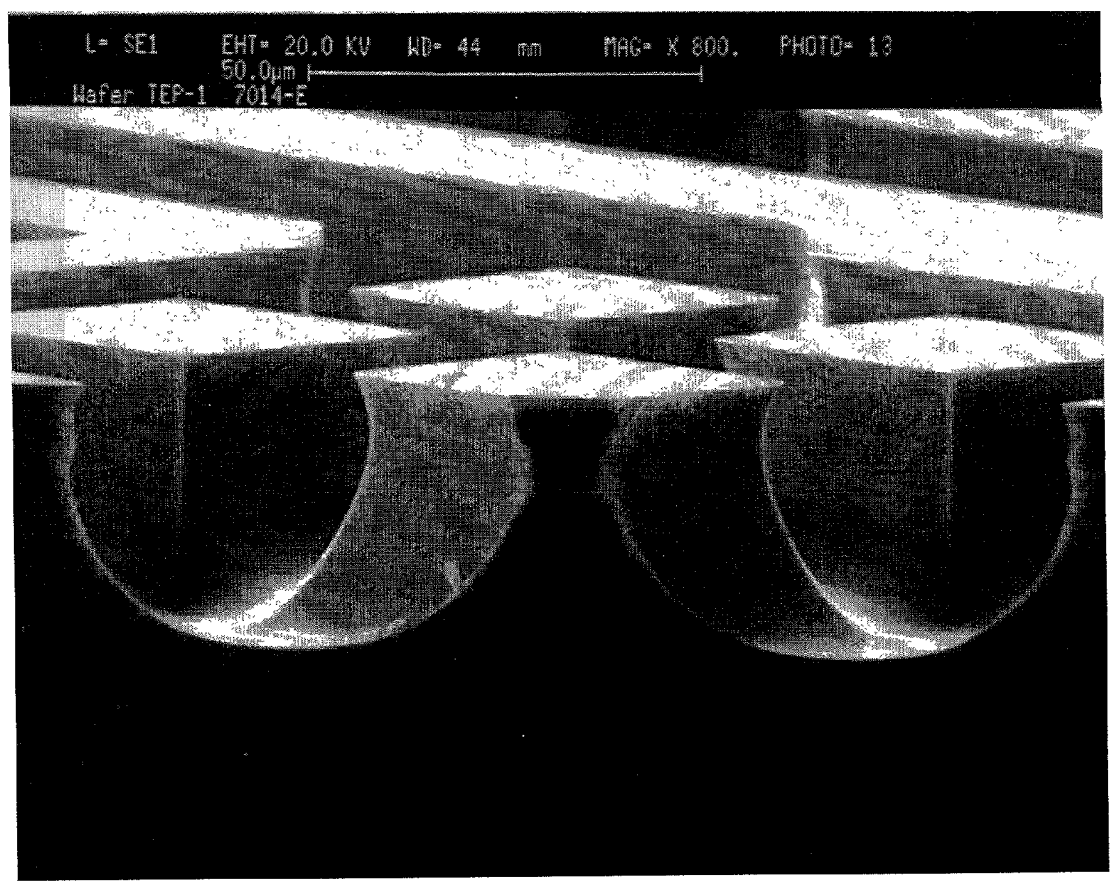
FIG. 9 is a scanning electron micrograph of sharp curves and corners due to etch behavior at intersections between channels.

Tissue growth can be greatly enhanced by engineering the geometry of channel profiles and intersections appropriately. Curvature and edge effects can be controlled in order to promote cell adhesion and prevent discontinuities or tearing of the forming tissue. In addition to etching process development, intersection geometries may be controlled (see, FIG. 9) by implementing specific design rules when laying out lithographic patterns. An excellent analogy to this methodology is given by the well-known micromachining tool known as fractal modeling (Kaandorp J A, *Fractal Modelling, Growth and Form in Biology* (Springer-Verlag, Berlin, 1994)), in which patterns are adjusted in advance by a predetermined amount based upon an understanding of the detailed etching behavior. This approach is exploited most fully when multi-level channel depths are invoked.

Multi-Level Channel Networks. To create multi-level channel networks, overlying masks are imprinted following planarization processes (Wolf S & Tauber R N, *Silicon Processing for the VLSI Era* (Lattice Press, Sunset Beach, Calif., 1986)), in which uneven surface topology is smoothed over by thick layers of photoresist or other materials. One of skill in the art would pay attention to the intersections between adjoining channels when multiple depths are superimposed on a single scaffold wafer.

A specific issue with glass wafer mold fabrication is that application of suitable maskingmaterials for glass etching warp the wafer. A new approach, using low-temperature mask-layer deposition methods, will be invoked to avoid warpage during processing. This approach significantly improves the adhesion of photoresist materials to the mask material covering the glass, reducing the loss of pattern fidelity and blurring of features.

Alternate Lithographic Processes. In one advantageous embodiment, we have used "negative molds" to produce biodegradable polymer scaffolds directly by casting techniques. A standard positive mold can be produced by etching a pattern (defined, for example, by the TEP-1 prototype vascular network pattern (see, FIG. 5) and be used to seed cells directly and form closed lumens. Layers of biodegradable polymers may be added to these mold surfaces, in order to provide structural integrity for layers of cells that may be lifted and folded from the silicon master (as described above).

Figure 10:
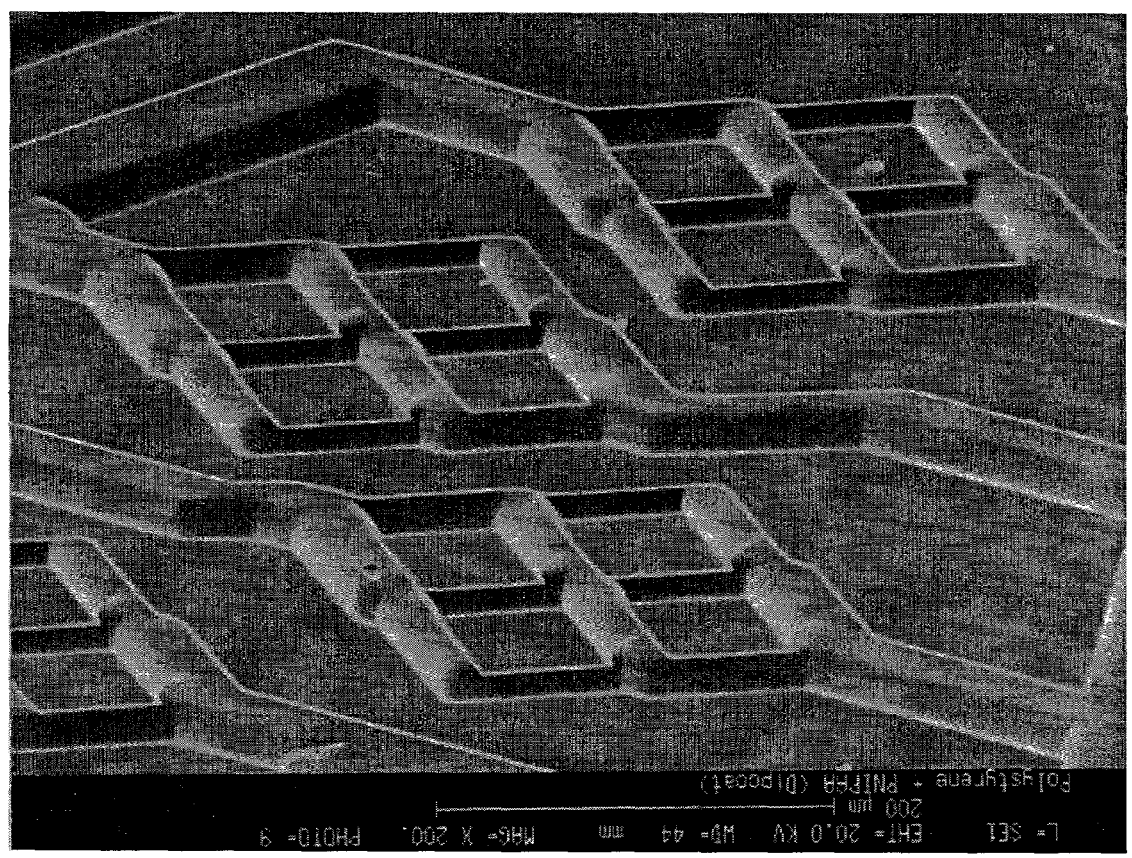
FIG. 10 is a scanning electron micrograph of a negative mold with channels raised.

However, we have established a process of "Image Reversal" that uses the same single lithographic master to produce etched patterns of opposing polarity (FIG. 10). This development results in substantial cost savings, which translates into shortened fabrication cycles and a more rapid pace of development. Use of the image reversal process reduces the number of expensive electron beam photomasks by a factor of two, and lowers the CAD mask generation time substantially as well.

We have addressed two challenges involved in demonstrating image reversal. The first challenge was the requirement for a photolithographic mask that reverses the image while maintaining the selectivity to plasma etching necessary to withstand the channel formation process. We achieved this dual requirement by invoking an image transfer process, in which the initial photolithographic layer that reversed the image is transferred into another, thicker layer for the etching process. Image reversal photoresists are typically only 1-2 microns thick; the layer used for this study was 1.4 microns in thickness. Such a layer will only withstand rounded-wall plasma etching to a depth of 5-10 microns; therefore, a thicker transfer layer was used to reach the 40 micron depth required for cell seeding The second challenge involved the etching itself, and the issues involved in etching the background field rather than the channels. A known difficulty with prior art methods of plasma etching is the "loading effect," in which the etch rate varies significantly as the fraction of wafer area available for etching is varied. The consequence of this phenomenon is that plasma etching properties shift radically as the percentage of open area increases. By contrast, for our negative mold, the fraction of open area increases from roughly 10% to 90%, slowing the etch rate sharply and altering the etch characteristics. Our process optimization resulted in the successful production of negative molds which could then be used to cast polymer templates with high-definition channels. Polymer casts maintain a remarkable quantitative similarity to the silicon masters used to produce them.

Polymeric scaffolds were formed by replica molding, using the silicon wafer as a master mold. Microfluidic chambers have been constructed from PDMS and other biocompatible polymers.

Method for Micromachining in Polymeric Material Using Thick Negative-Polarity Photoresist Technology. Newly invented photolithographic materials are sensitive to standard ultraviolet light rather than high-energy X-ray sources. One of these novel materials is an epoxy resin known as SU-8 (Zhang J et al., *J. Micromech. Microeng.* 11: 20 (2001)), which has been demonstrated to produce patterns 10 to 500 microns thick using ultraviolet lamps in a standard mask aligner. We have produced a wafer with a 250 micron thick layer of SU-8 applied directly to a silicon wafer substrate. We have produced SU-8 structures 200 microns in thickness with the TEP-1 pattern (FIG. 5); these molds capable of producing micropatterned polymer sheets.

A procedure for making a PDMS scaffold using Du Pont Sylgard and a SU-8 high aspect ratio negative photoresist is as follows: The materials used are SU-8 negative epoxy-based photoresist (Microchem Co.); a micromachined silicon wafer; a spinner; a hotplate; a UV exposure tool; a photomask; and a propylene glycol monomethyl ether acetate (PGMEA) organic solvent developer (also called XPS). To create the spin resist, cover ⅔ of the wafer radius with the SU-8 resist, and let the resist flow for 3-5 sec. Then, ramp the spinner at 100 rpm/sec to 500 rpm, and then instantaneously ramp to desired spin speed. The initial ramp allows spreading and wetting of the substrate surface. As a guide, the number after SU-8 (i.e. SU-8 50) indicates the resulting film thickness when spun at 2500 rpm. To softbake, place the micromachined wafer on a hotplate at room temperature and ramp slowly to 95° C., which is above the glass transition temperature. The hotplate should be planarized, because the resist will flow and correct some of the film imperfections (i.e. bubbles and topology). Because the resist is soft at 95° C., the film might pick up particles from the air. It is preferred to make a small covering for each wafer out of tin foil. Ramp to 95° C. and ramp down after 3 hours (using auto-off feature under button 8 on most commercial programmable hot plates). Then the resist is exposed to the micromachined wafer for 5-20 minutes. The nest step is a post exposure bake. Starting at room temperature, ramp to 95° C. with wafer on hot plate, as was done in softbake step. This time, bake for 1 hour. Finally, develop the polymeric material in PGMEA organic solvent. Mix gently but often. When almost completed, rinse in isopropyl alcohol. A white scum will likely appear, because dissolving SU-8 tends to stay at the surface of the wafer. Then, return to PGMEA bath for a minute. Repeat several times until the white scum is gone. There might still be organic residues when finished. To fully clean, rinse quickly in acetone, then quench in isopropyl alcohol. Remove the organic monomers in a quick distilled water rinse and quench once more with isopropyl alcohol. Dry with nitrogen gas.

Additional guidance is provided in EXAMPLE 3.

Figure 11:
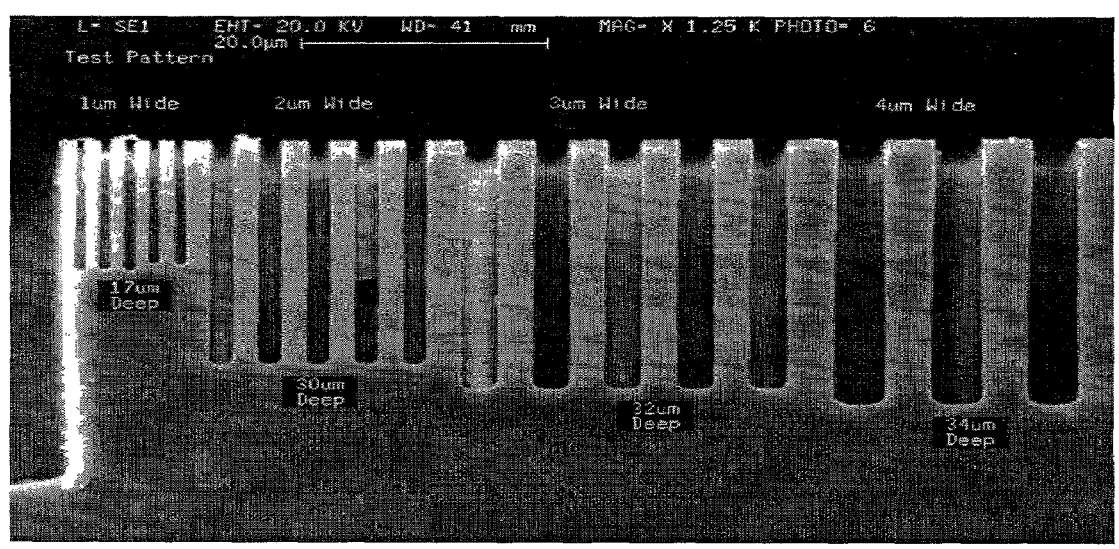
FIG. 11 is a scanning electron micrograph of a variety of varied-width and varied-height channels. The phenomenon by which narrower channels etch more slowly is called RIE lag.
Figure 12:
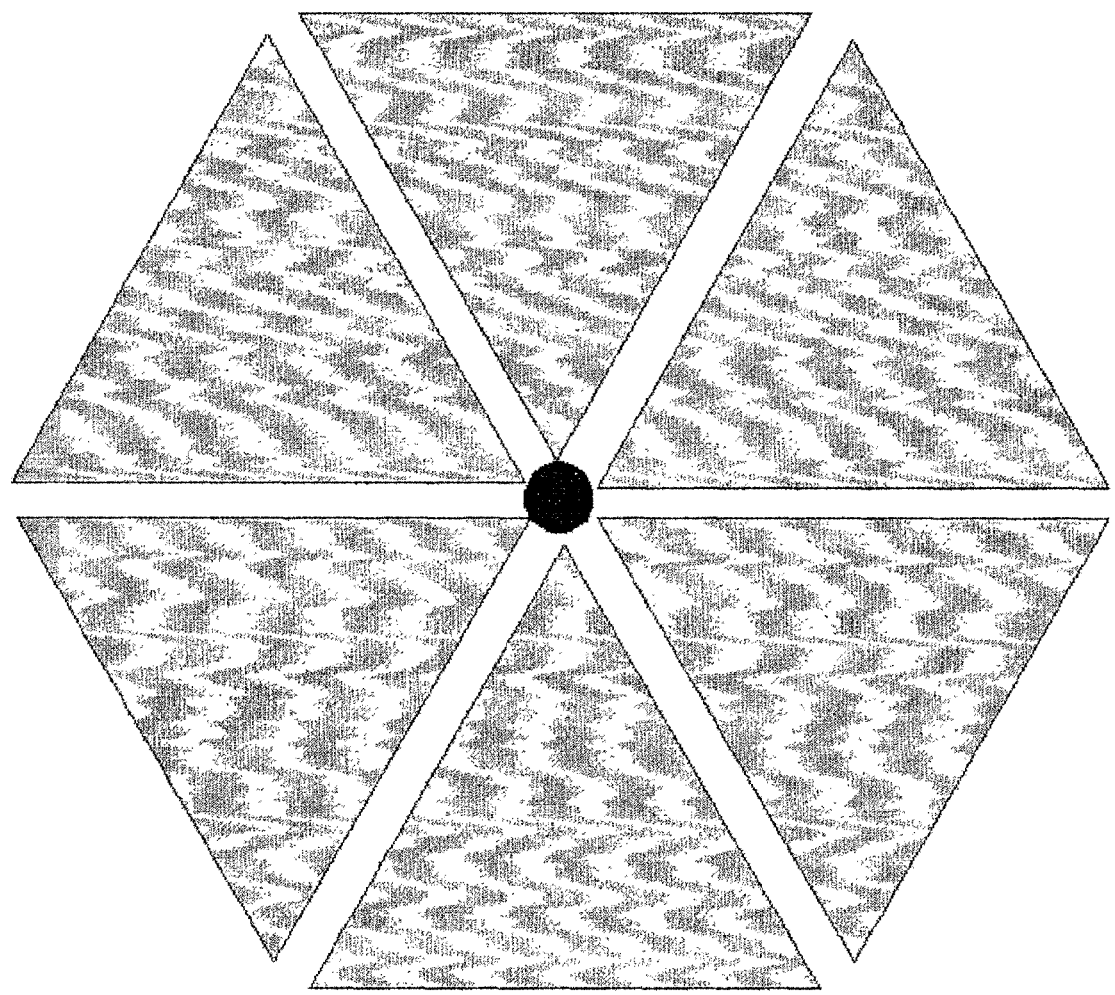
FIG. 12 is a schematic top drawing showing microfabricated units. The gray-shaded areas (shown here as triangles, although other shapes are possible) are coated with cell adhesion molecules, to promote the adhesion of cells (for example, hepatocytes). The white areas between the triangles are not coated with cell adhesion molecules, and so are open for colonization by cells that can for vascular tissue (for example, endothelial cells). The black circle in the middle is a vertical through-hole. The units shown in FIG. 12 are hexagons, but the units can be other shapes, for example, other regular polyhedrons, such as rectangles or pentagons.
Figure 13:
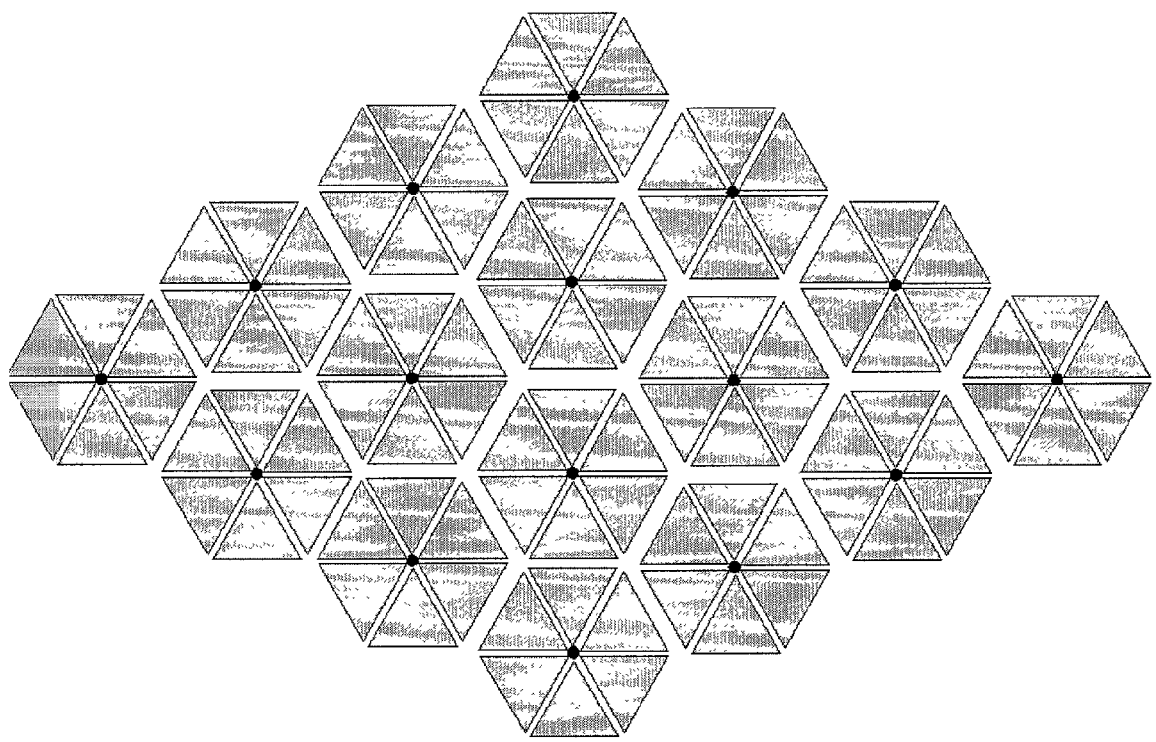
FIG. 13 is a schematic top drawing showing the packing of the microfabricated units in a horizontal arrangement on a microfabricated polymeric layer. The white areas between the units can have a greater width than the white areas between the triangles within the units. Other packing arrangements of the microfabricated units are possible.
Figure 14:
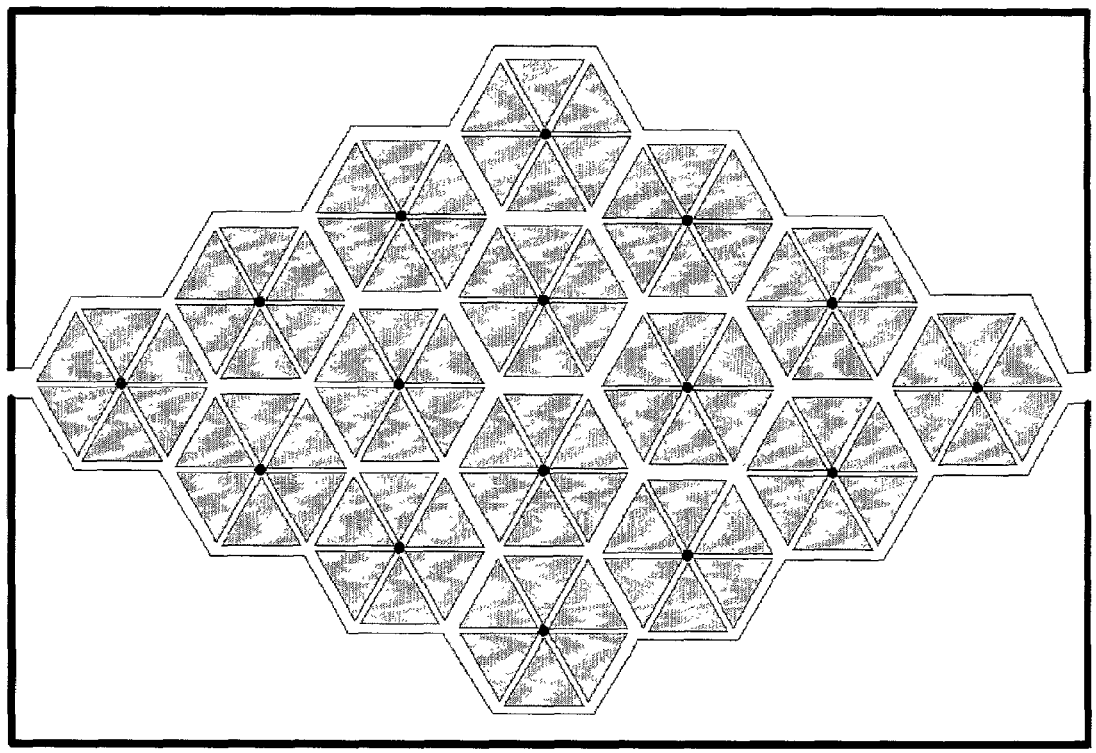
FIG. 14 schematic top drawing showing the packing of the microfabricated units on a microfabricated polymeric layer.
Figure 15:
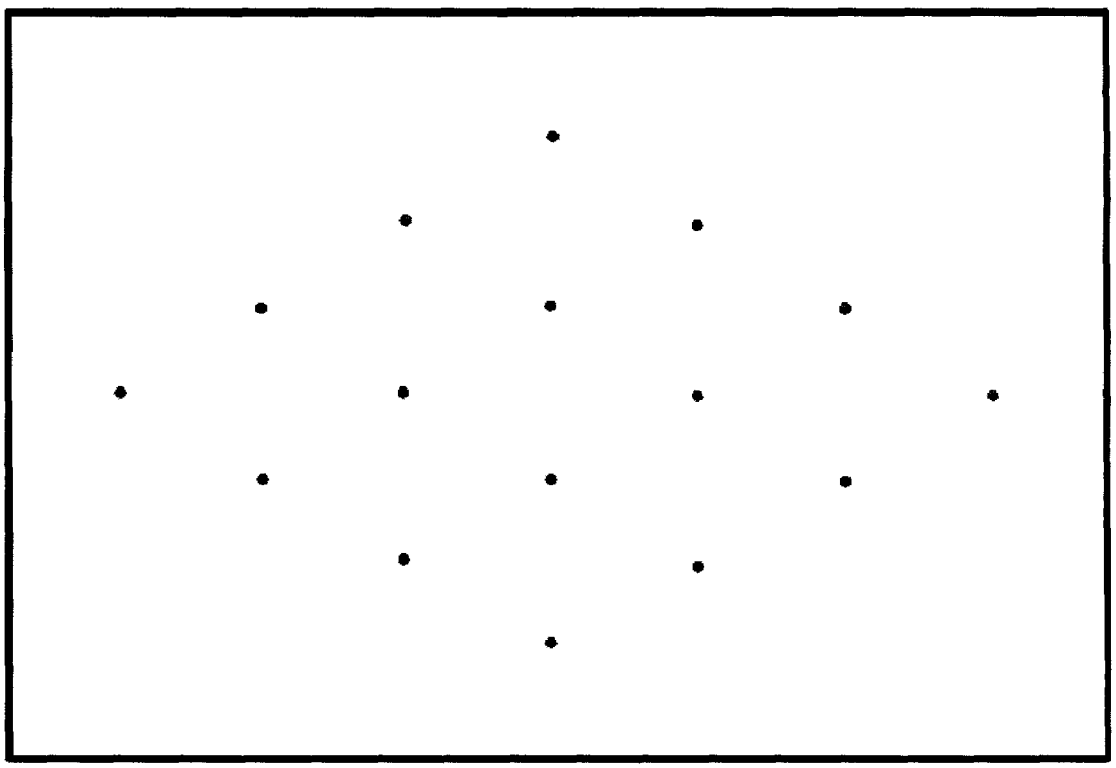
FIG. 15 schematic top drawing showing a polymeric layer without microfabrication. The black circle in the middle is a vertical through-hole.
Figure 16:
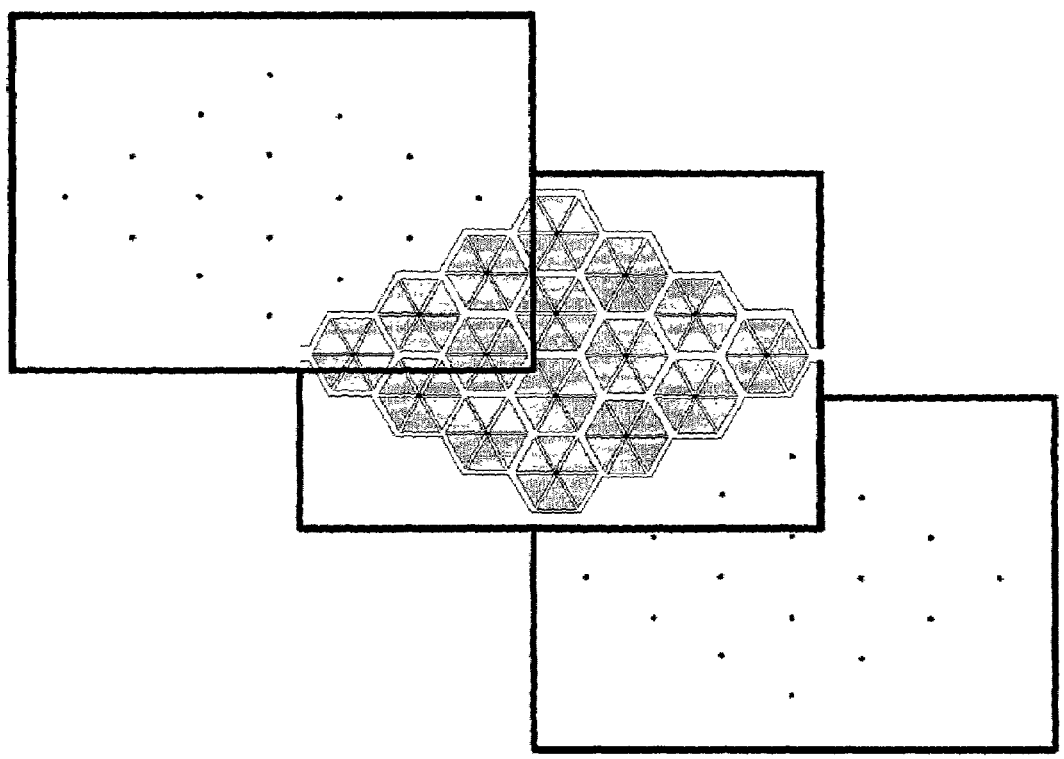
FIG. 16 schematic drawing showing the stacking of a microfabricated polymeric layer with polymeric layers without microfabrication. The black circles in each polymeric layer are vertical through-holes to be aligned.
Figure 17:
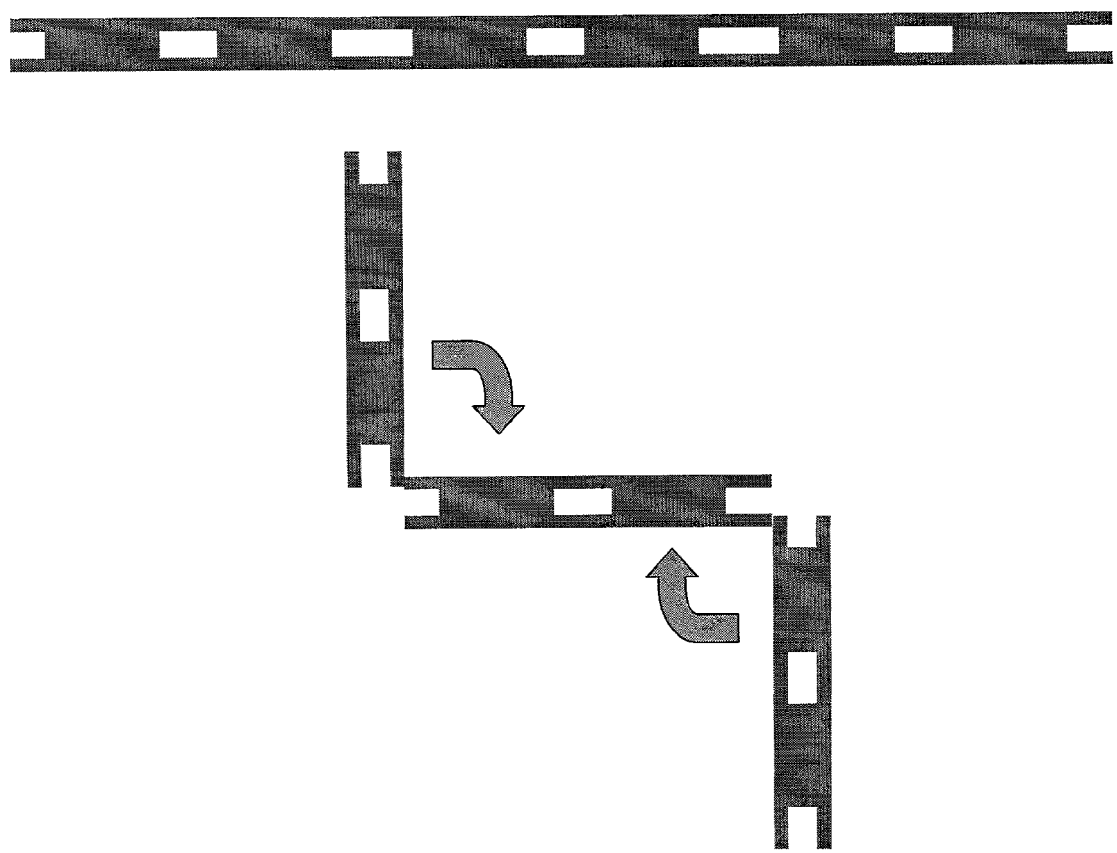
FIG. 17 is a schematic side drawing showing the extension into the third (z) dimension using a folding method. A long strip, sheet or roll of material is formed, and then folded as shown. Each section of the roll is a sheet of polymeric scaffold with closed lumens, or vessels. During folding, the sheet sections are folded such that the through-hole openings align, forming a vessel in the third (z) dimension.

Patterning Tall Structures and Multi-Level Tall Structures. We have successfully patterned epoxy resin materials to form tall structures (see, for example, FIG. 11). Extension of this approach to obtain multi-level tall structures provides molds with multiple channel depths from lithographic methods and other etch techniques. Multi-level tall structures can be obtained lithographically by techniques described herein.

Method for Micromachining in Polymeric Material Using Deep Reactive Ion Etching (DRIE). Polymeric materials can be micromachined using the technique of DRIE (Ayon A A et al., *Mat. Res. Soc. Symp. Proc.* 546: 51 (1999); Ayon A A et al., *J. Vac. Sci. Tech.* B 18: 1412 (2000)). Additional guidance is provided in EXAMPLE 3.

Stacking as an Approach to Achieving Three-Dimensionality. Extension of the two-dimensional technology into the third dimensions can be accomplished by stacking the two-dimensional layers on top of each other. This stacking method begins with many scaffold sheets produced by the molding, casting, embossing or other techniques described earlier. Once these scaffolds (nominally of the same size) are created, the sheets are lain down or bonded to other separate sheets of polymeric scaffold, atop one another. Each sheet has a closed network of lumens, or vessels. The sheets are connected by through-holes. The network of channels can differ or be similar to the previous layer, depending upon fluid mechanical considerations. In addition to the two-dimensional channels embedded in each layer, the through-holes can provide vessel structures that extend up into the third (vertical) dimension. Each successive layer could have slightly different patterns of through-holes, so that the effect would be to have vessels extending into the third dimension that are not necessarily precisely perpendicular to the plane of the sheet.

By extending this technology as needed, one can move from the presently achievable formation of small (~100 cm$^2$) sheets, each containing one plane of blood vessels, of polymeric scaffold, to the formation of perhaps 100 cm$^3$ of material, enough to build an organ. The process is low-cost, scalable, can be customized for the physiology of a particular patient, and is based upon currently available microfabrication technology.

Fastening the Stacked Layers. An aspect of this invention is the fastening or sealing of the polymeric layers. Preferably, the layers are irreversibly bound before implantation into the host. Depending on the composition of the layered material, the layers can be sealed by solvent bonding; reflow by heating (40° C.); treating surface with oxygen plasma; or by polymer flow at the surface. Biocompatible polymer materials may be bonded together by plasma activation to form sealed structures (Jo B-H & Beebe D J, *SPIE* 3877: 222 (1999)). The basic process results in bonded layers with channel architecture closely resembling that obtained with silicon etched molds.

Silicon-Glass Microfluidic Chambers to Test Sealing of Stacks. We have performed microfluidic tests that demonstrate that bonded structures are leakproof and support fluid pressures necessary for dynamic cell seeding. One of the most common methods used to seal micromachined wafers together is anodic bonding, a technique based on the high concentration of mobile ions in many glasses (Camporese D S et al., *IEEE Electron. Device Lett. EDL-2*, 61 (1981)). This process produces a permanent seal; fracture testing of silicon-glass anodically bonded interfaces produces a failure within the bulk of the glass.

Etched wafers may be bonded together, producing closed lumens suitable for fluidic experiments. We performed a fluidic test with a mixed-phase flow of alcohol with 10-micron fluorescent microspheres. An unetched glass capping layer was mechanically drilled for inlet and outlet fluid ports, and then anodically bonded to a silicon wafer plasma-etched with the TEP-1 (see, FIG. 5) geometry. A permanent seal with no leaks was produced, enabling one to obatain highly accurate pressure and flow data.

Alternatively, the multilayer device of the invention can be configured such that each of the layers has an alignment indentation on one surface of the layer and an alignment protrusion on the opposing surface of another layer. The alignment indentations shaped to mate with the alignment protrusion, so that the layers are held together.

Alternative Methods of Stacking. To build up the polymeric layers by mechanical assembly, the layers can be mechanically mated using biodegradable or non-biodegradable barbs, pins, screws, clamps, staples, wires, string, or sutures. See, U.S. Pat. No. 6,143,293. With this mechanical assembly approach, each prefabricated section can first be seeded with cells before assembly, and different scaffold materials, scaffold microstructure, and different cells can be placed in different sections of the scaffold. Thus, cells can be impregnated into scaffold sections before assembly, and can thus be can be embedded into the scaffold by assembling sections around these components. In addition, surface features on each scaffold subsection, which are readily fabricated, become part of the internal microstructure (e.g., molded surface channels become conduits for cell infusion, or for blood flow to stimulate angiogenesis). A surface feature on an individual scaffold segment will become an internal feature when another segment is assembled over it. For example, surface features such as channels can be micromachining into a first scaffold layer. When a second scaffold layer is placed atop that a first scaffold layer, the micromachined surface feature becomes an internal scaffold feature.

Stacking can also be accomplished as shown in FIG. 12 to FIG. 16. In one embodiment, the unit is a hexagon, but other unit shapes can be used, as well. The size of the unit can be from 100 microns to 1 mm. The size of the micromachined channels surrounding the units is about 50 microns in depth and width.

Various layers can have a micromachined closed network of lumens or vessels connected by through-holes. Each successive layer can have slightly different patterns of through-holes, so that the effect is to have vessels extending into the third dimension. The vessels in the third dimension are not necessarily precisely perpendicular to the plane of the sheet.

This alternative stacking technique uses the same micromachining procedure to produce biodegradable polymer layers with an intrinsic blood vessel network, but stacks them rather than utilizing the folding technique described above. Each layer can be superimposed upon the preceding layer and then bonded, using a variety of polymer layer bonding techniques. The network of channels can differ or be similar to the previous layer, depending upon fluid mechanical considerations. In addition to the two-dimensional (x, y) channels embedded in each layer, through-holes can provide vessel structures that extend up into the vertical (z) dimension.

Rollong or Folding as an Approach to Achieving Three-Dimensionality; Folding. An alternate method for achieving three-dimensionality is to generate a long strip of polymer scaffold material, which contains repeating units of the blood vessel network along with through-holes, and to fold the scaffold film in a z-fold fashion while aligning the through-holes to one another.

The rolling or folding process begins with the generation of a lengthy strip of polymer scaffold material, which contains a serial array of unit cells each of which is comprised of an array of channels mimicking the vascular network, produced from a wafer mold by molding, embossing, or the like. These unit cells may be identical or may be different. The units are linked to through-holes that provide the vertical channel connections between horizontal blood vessel layers. Once the polymeric scaffold strip has been formed, it is folded in a z-fold fashion (see, FIG. 4), and bonded together so that each fold is attached to the film portions above and below it with alignment to the through-holes.

This roll can be of a length to provide sufficient scaffolding material for an entire human organ, which can be hundreds or even more multiples of the area of a single wafer. Each section of the roll is a sheet of polymeric scaffold with closed lumens, or vessels. The vessels in each folded section of sheet are connected to a through-hole at the edge of the sheet (for example, one on each side, for inlet and outlet blood flow). During folding, the sheet sections are folded such that the through-hole openings align, forming a vessel in the third (z) dimension.

The roll can be in the shape of a spiral, helix, jelly roll or other cylindrically shaped objects.

Construction of Porous Devices Using Multiple Technologies. One approach to forming three-dimensional structures is to combine tissue specific cells with open porous polymer scaffolds, which can then be implanted. Large numbers of cells can be added to the polymer device in cell culture and maintained by diffusion. After implantation, vascular in-growth occurs, the cells remodel, and a new stable tissue is formed as the polymer degrades by hydrolysis. The diffusion distance for nutrients in vivo is only about 0.2 mm.

Porosity in the polymers can be created either at the level of the (micromachined) feature size (between 10 and 20 microns and greater) or at the sub-feature size level (at the level of the polymer itself, e.g., nanopores). At the level of the feature size, porosity is controlled by where the features are placed, and thus pore size and shape can vary in three dimensions. Porosity at a polymeric level can be created in a variety of ways known in the art.

In another embodiment of the invention, different scaffold structures, for example, those having different porosities for supporting differentiated cells, are provided. The mechanical assembly techniques of the present invention allow for both different types of cells to be seeded, as well as for different types of scaffolds to be used to fabricate heterogeneous generated tissue. See, U.S. Pat. No. 6,143,293.

The devices produced by MEMS technology can be coupled with Solid Freeform Fabrication (SFF) techniques such as Three Dimensional Printing (3DP) or micro-stereolithography to produce dense arrays of three-dimensional microstructures suitable for cell seeding, tissue formation, and implantation. For instance, micromolded films can be alternated with printed layers and bonded together to produce scaffolds with high porosity, three dimensionality, and embedded ultra-high-precision capillary beds.

Cell Addition, Cell Loading, and Cell Seeding onto the Scaffold. Cells for adding, loading or seeding to the multilayer device of the invention include endothelial cells, parenchymal cells (liver or kidney cells), bone marrow cells, osteoblasts, mesenchymal stem cells, satellite cells, or fibroblasts.

In one embodiment, two-dimensional structures are first used to provide an ordered array of branching channels to a polymer before epithelial cell seeding. After the epithelial cells are seeded, one can lift the channels formed from endothelial cells and combine them with layers of parenchymal tissue, such as hepatocytes. After combining and folding or stacking into three dimensions, when flow through the channels formed by the epithelial cells is initiated, then vascularized tissue will have been fabricated.

In another embodiment, cells can be loaded into the scaffold by the porous biodegradable polymer technology described in *Handbook of Microlithography, Micromachining and Microfabrication*, ed. P. Rai-Choudhury (SPIE Press, Bellingham, Wash., 1997). Pore formation can be accomplished using several techniques, including particulate leaching and microporous foam technology (Shastri V P et al., *Proceedings of the 1998 MRS Fall Meeting—Symposium on Biomedical Materials-Drug Delivery, Implants and Tissue Engineering*, Boston, Mass., USA, 1130 (1998); Griffith L G, in *Symp. HH, Tissue Engineering* (MRS, Fall 1998)). These techniques can be evaluated for compatibility with microfabrication by several criteria, such as (a) the tendency for pore formation to disturb the integrity of micromachined channel geometries, particularly the smallest capillaries; (b) impact of pore formation process on the ability to bond and stack layers; and (c) opportunities to avoid intersections between pores and channels, which is important for the evaluation of microfluidic effects.

In another embodiment, cells are added to the scaffold using the powerful technique of dynamic seeding. Dynamic seeding is accomplished by introducing cells through the inlet port of a sealed channel network, and adjusting flow and culture medium conditions so that the walls line with confluent tissue, but channels do not become occluded.

Further guidance to cell addition to scaffolds can be found in the EXAMPLES.

Cell Adhesion to Templates. Regions of initial cell adhesion in the microfabricated polymeric layers can be affected by modifying surface properties in select regions of the device, such as by printing a solution containing surface-active agents into the regions or lines in between where the binder is printed. A "surface-active agent" may be an agent that promotes cell adhesion, such as an RGD peptide (see below), or a material that inhibits cell adhesion, such as a surfactant, for example, polyethylene glycol or a pluronic™ (polypropylene oxide-polyethylene oxide block copolymers). Thus, cells can be positioned at specific sites in the matrix by using selective surface chemistries locally. For other methods and compositions for enhancing the bioadhesive properties of polymers using organic excipients, see U.S. Pat. No. 6,156,348.

As shown in FIG. 6 to FIG. 10, regions of the microfabricated polymeric layers can be treated or fabricated to increase cell adhesion for the first set of seeded cells (see gray areas). These regions can be made more adhesive to cells by the use of cell adhesion molecules. An adhesion peptide can be dissolved in water and printed into the "voids" using a set of printing nozzles.

Cell adhesion can be mediated by specific cell surface adhesion molecules (CAMs). There are many different families of CAMs, including the immunoglobulin, integrin, selectin and cadherin superfamilies, and each cell type expresses a unique combination of these molecules. Many cell adhesion molecules and fragments of cell adhesion molecules are known in the art and have been used to cause cells to adhere to polymeric surfaces. Pigot & Power, *The Adhesion Molecule Facts Book*. (London, Academic Press, 1993). The particular cell adhesion molecule or fragment of cell adhesion molecule that is to be used in the region of initial cell adhesion depends on the cell population to be attached. Cells that attach to fibronectin can be made to attach by coating the regions of initial cell adhesion with fibronectin, with a peptide (such as argininge-glycine-aspartic acid; RGD) that binds to a fibronectin receptor on the first set of seeded cells, or by an engineered protein that binds to the fibronectin receptor, such as ProNectin® F, a protein polymer that incorporates multiples copies of the RGD cell attachment ligand of human fibronectin interspersed between repeated structural peptide segments (Protein Polymer Technologies Inc., San Diego, Calif., USA; see U.S. Pat. No. 5,514,581). Cells that attach to laminin can be made to attach by coating the regions of initial cell adhesion with laminin, with a peptide (such as IKVAV) that binds to a fibronectin receptor on the first set of seeded cells, or by an engineered protein that binds to the laminin receptor, such as ProNectin® L, a protein polymer that incorporates multiples copies of the IKVAV cell attachment ligand of human laminin alpha chain interspersed between repeated structural peptide segments (Protein Polymer Technologies Inc., San Diego, Calif., USA; see U.S. Pat. No. 5,211,657). Alternatively, the regions of initial cell adhesion can be coated with combinations of extracellular matrix molecules, such as laminin, fibronectin, collagens, vitronectin, entactin and tenascin, or with ProNectin® F Plus, which combines elements of the functionality of fibronectin, collagen, and polylysine. Peptides to which cells can adhere include Arg-Gly-Asp (RGD), which is bound by integrins (see Cardarelli et al., *J. Biol. Chem.* 267: 23159-64 (1992); Tyr-Ile-Gly-Ser-Arg (YIGSR), which is bound by α6β1 integrin; KYSFNYDGSE, which is bound by the neural cell adhesion molecule N-CAM; or the N-CAM heparin sulfate-binding site IWKHKGRDVILKKDVRF. Other cell adhesion molecules can be used that more specifically target the first set of seeded cells. For example, the regions of initial cell adhesion can be coated with a hepatocyte cell-cell adhesion molecule (C-CAM; Cell-CAM 105) which is a cell surface glycoprotein that is involved in cell-cell adhesion of rat hepatocytes in vitro and when immobilized on a solid surface). Tingstrøm et al., *J. Cell Sci.* 96: 17-25 (1990). Such cell adhesion peptides also include REDV (for endothelial cells) or galactose (for hepatocytes), optionally linked to a strong hydrophobic moiety (such as than in Cell-Tak, a commercially available reagent), which adsorb strongly to the surface of the polymeric material. This differentiation of cell adhesion allows spatial segregation when seeding more than one cell type at the initial time.

Alternatively, the regions of initial cell adhesion can be machined using polymer into which the desired cell adhesion molecule has been included. See, U.S. Pat. No. 5,514,581; see also, the SmartPlastic® line of tissue culture labware (Protein Polymer Technologies Inc., San Diego, Calif., USA), which features a culture surface which has been activated with ProNectin® F Cell Attachment Factor.

The polymeric surface can also be modified to prevent cellular adhesion. This may be desirable to prevent excessive soft connective tissue in-growth into the device from the surrounding tissue, and can be accomplished, for example, by printing an aqueous solution of a pluronic™ (BASF) or poloxamer™ in the voids (the white areas in FIG. 12). The hydrophobic block of such copolymers will adsorb to the surface of the channels, with the hydrophilic block extending into the aqueous phase. Surfaces with adsorbed pluronics™ resist adsorption of proteins and other biological macromolecules. Other adhesion-preventing materials are described in Lee et al., *J. Biomed. Mat. Res* 23: 351-368 (1989).

Printing the device with surface active agents while the "walls" of the device are still "wet" with organic solvent (such as chloroform) can enhance the adsorption of the adhesion-preventing material to the walls and can even allow the hydrophobic block to become blended into the surface, enhancing the stability of the resulting surface modification.

Other additives suitable for use with the invention include biologically or pharmaceutically active compounds, for example, biologically active ligands, and substances that enhance or exclude particular varieties of cellular or tissue ingrowth. Such substances include, for example, osteoinductive substances, such as bone morphogenic proteins (BMP), epidermal growth factor (EGF), fibroblast growth factor (FGF), platelet-derived growth factor (PDGF), insulin-like growth factor (IGF-I and II), TGF-β and the like.

Cell Seeding. After the scaffold with the desired high degree of micromachining is prepared, the scaffolds are seeded with the desired cells or sets of cells. The distribution of cells throughout the scaffolds can influence both (1) the development of a vascularized network throughout the scaffold, and (2) the successful integration of the vascular device with the host. The approach used in this invention is to provide a mechanism for the ordered distribution of cells onto the scaffold. Cells can be seeded onto the scaffold that are enriched for extracellular matrix molecules or peptides that enhance cell adhesion. Cells can be seeded onto the scaffold in an ordered manner using methods known in the art, for example, Teebken et al., *Eur. J. Vasc. Endovasc. Surg.* 19(4): 381-6 (April 2000); Ranucci et al., *Biomaterials* 21(8): 783-93 (April 2000). Also, tissue-engineered devices can be improved by seeding cells throughout the polymeric scaffolds and allowing the cells to proliferate in vitro for a predetermined amount of time before implantation, using the methods of Burg et al., *J. Biomed. Mater. Res.* 51(4): 642-9 (Sep. 15, 2000).

The scaffold is first seeded with a layer of parenchymal or hepatocyte cells. This layer can be maintained in culture for a week or so in order to obtain a population doubling. It can be maintained in a perfusion bioreactor to ensure adequate oxygen supply to the cells in the interior. The device is then seeded with a layer of endothelial cells and cultured further. In regions where the matrix is resorbed rapidly, the tissue can expand and become permeated with capillaries that grow from the conduits in the center of the shaded area.

Cell Seeding of Horizontal Layer by Laminar Flow. Sets of cells can be added to or seeded into the joined or fastened scaffolds, so that the three-dimensional scaffolds can be a template for cell adhesion and growth by the added or seeded cells. The added or seeded cells can be parenchymal cells, such as hepatocytes. A second set of cells (such as endothelial cells) can be added to or seeded onto the assembled scaffold system through other vessels than those used to seed the first set of cells. The cell seeding is performed by slow flow. As a practical matter, the geometry of the polymer layers will determine the flow rates. In general, endothelial cells can enter and form vessel walls in micromachined channels that are 10-50 microns. Thus, in addition to serving as a mechanical framework for the organ, the assembled scaffold system provides a template for all of the microstructural complexity of the organ, so that cells have a mechanical map to locate themselves and form subsystems, such as blood vessels in the liver.

In one embodiment, different sets of cells are seeded onto different polymer layers of the assembled scaffold system, both in the horizontal layer (see, for example, FIG. 19 to FIG. 22). In another embodiment, the different sets of cells are seeded onto polymer scaffold using pores or channels from different directions (see, for example, FIG. 12 to FIG. 16). Various combinations are also possible.

Channels in the horizontal direction proceed from larger to smaller to larger. The geometries can be as complex as desired in-plane (horizontal direction). Thus, one can use small geometries in-plane (such as horizontal conduits 5-20 microns).

However, the vertical conduits need not go from larger to smaller to larger. In the vertical direction, the vertical conduits are typically parallel to each other. The vertical conduits can be on the micron level, large enough only to allow cell seeding (e.g., hepatocytes are about 40 microns).

Cells to be Seeded onto the Scaffold. Preferred cell types are mesenchymal cells, especially smooth or skeletal muscle cells, myocytes (muscle stem cells), fibroblasts, chondrocytes, adipocytes, fibromyoblasts, and ectodermal cells, including ductile and skin cells, hepatocytes, Islet cells, cells present in the intestine, and other parenchymal cells, osteoblasts and other cells forming bone or cartilage. Cells to be implanted are dissociated using standard techniques such as digestion with a collagenase, trypsin or other protease solution. In some cases it may also be desirable to include nerve cells. Cells can be normal or genetically engineered to provide additional or normal function.

Cells are preferably autologous cells, obtained by biopsy and expanded in culture, although cells from close relatives or other donors of the same species may be used with appropriate immunosuppression. Immunologically inert cells, such as embryonic or fetal cells, stem cells, and cells genetically engineered to avoid the need for immunosuppression can also be used. Methods and drugs for immunosuppression are known to those skilled in the art of transplantation.

Cells are obtained by biopsy and expanded in culture for subsequent implantation. Cells can be easily obtained through a biopsy anywhere in the body, for example, skeletal muscle biopsies can be obtained easily from the arm, forearm, or lower extremities, and smooth muscle can be obtained from the area adjacent to the subcutaneous tissue throughout the body. The biopsy specimen is then transferred to the lab where the muscle can be grown utilizing the explant technique, wherein the muscle is divided into very pieces that are adhered to culture plate, and serum containing media is added. Alternatively, the muscle biopsy can be enzymatically digested with agents such as trypsin and the cells dispersed in a culture plate with any of the routinely used medias. After cell expansion within the culture plate, the cells can be easily passaged utilizing the usual technique until an adequate number of cell is achieved.

The hepatocytes added to the multicellular devices of the invention can be highly proliferative hepatocytes, known as small hepatocytes (SHCs), which have the ability to proliferate in vitro for long periods of time (Mitaka T et al., *Biochem Biophys Res Commun* 214: 310-317 (1995); Taneto C & Yoshizato K, *Am J Pathol* 148: 383-392 (1996)). Small hepatocytes express hepatocyte specific functions such as albumin production (Mitaka T et al., *Hepatology* 29: 111-125 (1999)). We have investigated the survival and function of small hepatocytes when co-cultured on three-dimensional microporous biodegradable polymer scaffolds under dynamic culture conditions (EXAMPLE 3).

Measurement of Fluid Dynamics. Fluid flow measurements characterize the distribution, pressure drops and flow rates of liquid in each region of the micromachined tissue engineering wafers have been initiated. These measurements can be based on simple fluid mechanical models which have been adapted for the particular channel and flow network configurations used in this work. The general approach used in the fluid mechanical tests invokes electrical networks to represent pressure drops in the vascular networks. For all but the largest vessels, fluid flow is well within the laminar regime, with Reynolds Numbers on the order of unity. This greatly simplifies the analysis, since the Hagen-Pouseuille Law can be applied to the pressure drop for fluid flow in a pipe. Generally, the profile of the channels micromachined using the techniques described herein is much closer to rectangular than to cylindrical. An expression containing a series expansion is inserted in place of the simple Hagen-Pouseuille fourth-power relation to compute pressure drop in these rectangular channels. Combinations of series and parallel channels are then represented as resistors, with simple algebraic expressions to calculate the net pressure differential between any two points. This type of analysis has been used to predict fluid velocity as a function of pressure to a very high degree of accuracy. We have performed tests with fluorescent dye solutions to determine the flow patterns. Fluorescent beads were added to the solution as a model system for the behavior of red blood cells in the narrow channels.

One bioreactor design consists of two major components: a round, stainless steel base machined to fit a wafer (or other device of the invention) and create even compression, and a clear lexan cover designed with an input and output and to allow microscopic viewing. The wafer (or other device of the invention) is evenly pressed against a silicone rubber and fluid is passed through the wafer. Pressure and fluid flow measurements are possible at the input and output sites. Cells are introduced into the system through either dynamic flow seeding through the bioreactor or by seeding the wafer with cells before sealing with the silicone rubber.

Microfluidic structures can be passive elements only, such as channels of varying width and depth. However, the invention encompasses the use of active devices such as wafer-scale arrays of micropumps and microvalves, produced using silicon micromachining processes similar to those used to fabricate the channel arrays, within the channel networks. Local control of pressure and flow can be obtained by using such active devices in the bioreactor.

Measurements of the microfluidic behavior of the channel networks are used to confirm the validity of the prediction for cell seeding in the various configurations (see, EXAMPLE 3).

Uses of the Invention. This invention can provide replacement organs for individuals with damaged or failing organs, using the host's cellular material to substantially reducing or eliminating the high morbidity and mortality rates associated with the insufficient supply of donor organs. Devices may include a series of bioartificial devices to support kidney, liver, and other organ functions. The devices can be implanted into a recipient by methods well known in the surgical arts. Further guidance to implantation is provided in EXAMPLE 1.

Other uses of the invention include use as biodegradable scaffolds for tissue engineering, biodegradable or biocompatible life assist and biohybrid artificial organs and tissues. The artificial organs of the invention have a specific macroscopic shape that can be fashioned to the specific needs of a patient. The artificial organ of the invention may be fabricated (prior to cell seeding) into useful articles for tissue engineering and tissue-guided regeneration applications, including reconstructive surgery. The artificial organ should be rigid enough to maintain the desired shape under in vivo conditions. Engineering of strong, pliable tissues is discussed in U.S. Pat. No. 5,855,610.

Such devices can be extracorporeal, due to size considerations, may provide partial support function, may extend the time between hospital treatments for patients on chronic organ support therapies, and will improve the quality of life between hospital treatments. Current extracorporeal devices do not incorporate the precise microfabrication capabilities offered by MEMS technology, and therefore function is limited by the resolution limits of current hollow fiber and membrane fabrication methods. Insertion of MEMS technology into this domain is expected to have major benefits for hemofiltering, dialysis and other applications.

Still other uses of the invention include drug delivery devices, assay systems and test devices for modeling cell attachment. Currently available test methods lack the precision necessary to guide cell movement on the microscale. By this invention, micromachined grooves direct the orientation of cells and control their speed along surfaces, and can therefore be used to enhance the growth of confluent layers of tissue. Physicomechanical properties such as shear modulus may be enhanced and tested by directing cell behavior utilizing micromachining.

Cell-based sensor technologies can also provided from tissue-engineered templates created for this program. The low-cost of batch-fabricated MEMS technology is an advantage for instant response test kits. Such diagnostic tools can be throwaway, utilize small quantities of body fluid, incorporate measurement and analytical capabilities in a single processor, and be very low cost. Microfluidic technology such as flow dynamics, channel formation and sealing methods, and three-dimensional network formation processes, are highly transferable to sensing and diagnostic applications. See, published PCT patent application WO 99/47922, incorporated herein by reference.

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented in order to more fully illustrate the preferred embodiments of the invention. These examples should in no way be construed as limiting the scope of the invention, as defined by the appended claims.

EXAMPLE 1

Silicon Micromachining to Tissue Engineer Branched Vascular Channels for Liver Fabrication Templates for the formation of sheets of living vascularized tissue were fabricated using micromachining technology. For this EXAMPLE, a single level etch was used to transfer a vascular network pattern into an array of connected trenches in the surface of either or silicon and glass wafers.

Micromachining Techniques. A simple geometry was selected for patterning the vascular network. Near the edge of each wafer, a single inlet or outlet was positioned, with a width of 500 µm. After a short length, the inlet and outlet branched into three smaller channels of width 250 µm; each of these branched again into three 125 µm channels, and finally down to three 50 µm channels. From the 50 µm channels extends the capillary network, which comprises the bulk of the layout. Between these inlet and outlet networks lies a tiled pattern of diamonds and hexagons forming a capillary bed and filling the entire space between the inlet and outlet. In one configuration, the capillary width was set at 25 µm; in the other capillaries were fixed at 10 µm. This geometry was selected because of its simplicity as well as its rough approximation to the size scales of the branching architecture of the liver.

Layout of this network was accomplished using CADENCE software (Cadence, Chelmsford, Mass., USA) on a Silicon Graphics workstation. A file with the layout was generated and sent electronically to Align-Rite (Burbank, Calif., USA), where glass plates with electron-beam-generated patterns replicating the layout geometry were produced and returned for lithographic processing.

Starting materials for tissue engineering template fabrication were standard semiconductor grade silicon wafers (Virginia Semiconductor, Powhatan, Va., USA), and standard Pyrex® wafers (Bullen Ultrasonics, Eaton, Ohio, USA) suitable for MEMS processing. Silicon wafers were 100 mm diameter and 525 microns thick, with primary and secondary flats cut into the wafers to signal crystal orientation. Crystal orientation was <100>, and wafers were doped with boron to a resistivity of approximately 5 $\Omega$-cm. The front surface was polished to an optical finish and the back surface ground to a matte finish. Pyrex® wafers were of composition identical to Corning 7740 (Corning Glass Works, Corning N.Y.), and were also 100 mm in diameter, but had a thickness of 775 microns. Both front and back surfaces were polished to an optical finish. Prior to micromachining, both wafer types were cleaned in a mixture of 1 part $H_2SO_4$ to 1 part $H_2O_2$ for 20 minutes at 140° C., rinsed 8 times in deionized water with a resistivity of 18 M$\Omega$, and dried in a stream of hot $N_2$ gas.

For silicon and Pyrex® wafers, standard photolithography was employed as the etch mask for trench formation. Etching of Pyrex® wafers requires deposition of an intermediate layer for pattern transfer which is impervious to the etch chemistry. A layer of polysilicon of thickness 0.65 µm over the Pyrex® was utilized for this purpose. This layer was deposited using Low Pressure Chemical Vapor Deposition (LPCVD) at 570° C. and 500 mTorr via the standard silane decomposition method. In the case of silicon, photoresist alone could withstand limited exposure to two of the three etch chemistries employed. For the third chemistry, a 1.0 µm layer of silicon dioxide was thermally deposited at 1100° C. in hydrogen and oxygen.

Once the wafers were cleaned and prepared for processing, images of the prototype branching architecture were translated onto the wafer surfaces using standard MEMS lithographic techniques. A single layer of photoresist (Shipley 1822, MicroChem Corp., Newton, Mass., USA) was spun onto the wafer surfaces at 4000 rpm, providing a film thickness of approximately 2.4 µm. After baking at 90° C. for 30 minutes, the layer of photoresist was exposed to uv light using a Karl Suss MA6 (Suss America, Waterbury, Vt., USA) mask aligner. Light was passed through the lithographic plate described earlier, which was in physical contact with the coated wafer. This method replicates the pattern on the plate to an accuracy of 0.1 µm. Following exposure, wafers were developed in Shipley 319 Developer (MicroChem Corp., Newton, Mass., USA), and rinsed and dried in deionized water. Finally, wafers were baked at 110° C. for 30 minutes to harden the resist, and exposed to an oxygen plasma with 80 Watts of power for 42 seconds to remove traces of resist from open areas.

Silicon wafers were etched using three different chemistries, while Pyrex® wafers were processed using only one technique. For Pyrex®, the lithographic pattern applied to the polysilicon intermediate layer was transferred using a brief (~1 minute) exposure to $SF_6$ in a reactive-ion-etching plasma system (Surface Technology Systems, Newport, United Kingdom). Photoresist was removed, and the pattern imprinted into the polysilicon layer was transferred into trenches in the silicon using a mixture of 2 parts $HNO_3$ to 1 part Hf at room temperature. With an etch rate of 1.7 microns per minute, 20 micron deep trenches were etched into the Pyrex® wafers in approximately 12 minutes. Since the chemistry is isotropic, as the trenches are etched they become wider. Processing with the layout pattern with 25 µm wide capillary trenches tended to result in merging of the channels, while the use of 10 µm wide trenches avoided this phenomenon. Interferometric analysis of the channels after etching showed that surface roughness was less than 0.25 µm. Once channel etching of Pyrex® wafers was completed, polysilicon was removed with a mixture of 10 parts $HNO_3$ to 1 part HF at room temperature, and wafers were re-cleaned in 1 part $H_2SO_4$ to 1 part HF.

Three different chemistries were employed to etch silicon in order to investigate the interaction between channel geometry and cell behavior. First, a standard anisotropic plasma etch chemistry, using a mixture of $SF_6$ and $C4F_8$ in a switched process plasma system from STS, was used to produce rectangular trenches in silicon. Narrower trenches are shallower than deep trenches due to a phenomenon known as RIE lag (see, FIG. 11).

A second process utilized a different plasma system from STS, which produces isotropic trenches with a U-shaped profile. While the process is isotropic, widening of the trenches is not as severe as is experienced in the isotropic Pyrex® etching process described earlier. In both of these plasma-etching cases, trenches were etched to a nominal depth of 20 µm.

For the third process, anisotropic etching in KOH (45% w/w in $H_2O$ at 88° C.), the intermediate silicon dioxide layer described above was used. First, the silicon dioxide layer was patterned using HF etching at room temperature. The KOH process produces angled sidewalls rather than the rectangular profile or U-shaped profile produced by the first two recipes, respectively. Crystal planes in the <111> orientation are revealed along the angled sidewalls, due to anisotropic properties of the KOH etch process as a function of crystal orientation. Due to the self-limiting nature of the channels produced by this process, trench depth was limited to 10 µm. After completion of the silicon wafer etching, all layers of photoresist and silicon dioxide were removed, and wafers were cleaned in 1 part $H_2SO_4$: 1 part $H_2O_2$ at 140° C., followed by rinsing in deionized water and drying in nitrogen gas. This process resulted in excellent adhesion and enhanced lifting of living tissue, as described below.

For this set, no attempt was made to alter the surface chemistry of the silicon and Pyrex® wafers. Prior to processing, silicon wafers were uniformly hydrophobic, while Pyrex® wafers were equally hydrophilic, as determined by observations of liquid sheeting and sessile drop formation. After processing, unetched surfaces appeared to retain these characteristics, but the surface chemistry within the channels was not determined.

Animals. Adult male Lewis rats (Charles River Laboratories, Wilmington, Mass., USA), weighing 150-200 g, were used as cell donors. Animals were housed in the Animal Facility of Massachusetts General Hospital in accordance with NIH guidelines for the care of laboratory animals. They were allowed rat chow and water ad libitum and maintained in 12-hour light and dark cycle.

Hepatocyte Isolation. Male Lewis rats were used as hepatic cell donors. Hepatocytes were isolated using a modification of a two-step collagenase perfusion procedure. Briefly, the animals were anesthetized with Nembutal Sodium Solution (Abbott Laboratories, North Chicago, Ill., USA), 50 mg/kg, and the abdomen was prepared in sterile fashion. A midline abdominal incision was made and the infrahepatic inferior vena cava was cannulated with a 16-gauge angiocatheter (Becton Dickinson). The portal vein was incised to allow retrograde efflux and the suprahepatic inferior vena cava was ligated. The perfusion was performed at a flow rate of 29 ml/min initially with a calcium-free buffer solution for 5 to 6 minutes, then with a buffer containing collagenase type 2 (Worthington Biomedical Corp., Freehold, N.J., USA) at 37° C. The liver was excised after adequate digestion of the extracellular matrix and mechanically agitated in William's E medium (Sigma, St. Louis, Mo., USA) with supplements to produce a single cell suspension. The suspension was filtered through a 300 µm mesh and separated into two fractions by centrifugation at 50 g for 2 minutes at 4° C. The pellet containing the viable HC fraction was resuspended in William's E medium and further purified by an isodensity Percoll centrifugation. The resulting pellet was then resuspended in a Hepatocyte Growth Medium, and cell counts and viabilities of hepatocytes were determined using the trypan blue exclusion test. Hepatocyte Culture Medium is as follows: William's E medium supplemented with 1 g sodium pyruvate (Sigma, St. Louis, Mo., USA) and 1% glutamine-penicillin-streptomycin (Gibco BRL, Gaithersburg, Md.) were used during the cell isolation process. The plating medium was Dulbecco's modified eagle medium (Gibco BRL) supplemented with 10% fetal bovine serum, 1% penicillin-streptomycin, 44 mM sodium-bicarbonate, 20 mM HEPES, 10 mM niacinamide, 30 µg/ml L-proline, 1 mM ascorbic acid 2 phospate, 0.1 µM dexamethasone (Sigma), insulin-transferrin-sodium selenite (5 mg/L-5 mg/L-5 µg/L, Roche Molecular Biomedicals, Indianapolis, Ind., USA), and 20 ng/ml epidermal growth factor (Collaborative Biomedical Products, Bedford, Mass., USA).

Additional guidance to hepatocyte isolation and culture is found in Griffith et al., *Ann. N.Y. Acad. Sci.* 831: 382-97 (Dec. 31, 1997) and Kaufmann et al., *Transplant Proc.* 31(4): 1928-9 (June 1999). Hepatocytes are about 40 microns.

Endothelial Cell Culture Medium. The endothelial cells were derived from rat lung microvessels and they were purchased directly from the vendor, Vascular Endothelial Cell Technologies (Rensselaer, N.Y., USA). Dulbecco's modified eagle medium (Gibco BRL) was supplemented with 10% fetal bovine serum, 1% penicillin-streptomycin, 25 mg of ascorbic acid (Sigma), 10 mg L-alanine (Sigma), 25 mg L-proline (Sigma), 1.5 µg cupric sulfate (Sigma), glycine (Sigma) and 1M Hepes buffer solution (Gibco BRL). The media was supplemented with 8 mg of ascorbic acid every day.

For additional guidance for endothelial cell culture, see, Bordenave et al., *Endothelium* 6(4): 267-75 (1999).

Cell Attachment and Lifting from Non-Etched Silicon and Pyrex® Wafers. Silicon and Pyrex® were both tested as possible substrates for the culture and lifting of endothelial cells and hepatocytes. Before cell seeding, the Pyrex® wafers were sterilized with 70% ethanol overnight and washed three times with sterile phosphate buffered saline (Gibco BRL). Silicon wafers were first soaked in acetone for 1 hr, followed a methanol rinse for 15 minutes, and overnight sterilization in 100% isopropyl alcohol. Rat lung microvascular endothelial cells was cultured on non-coated Pyrex® and silicon surfaces, as well as wafers coated with vitrogen (30 µg/ml), Matrigel® (1%), or gelatin (10 mg/ml). Once isolated, the cells were resuspended in endothelial cell culture medium, seeded uniformly onto the wafer at a density of $26.7 \times 10^3$ cells/cm$^2$, and cultured at 5% $CO_2$ and 37° C. After reaching confluence, we tested the ability for the monolayer of endothelial cells to lift from the wafers using a cell scrapper to promote detachment.

The rat hepatocytes were also cultured on non-coated Pyrex® and silicon, as well as wafers coated with a thin and thick layers of vitrogen (30 µg/ml and 3 µg/ml) and Matrigel (1%) in order to determine the optimal methods for lifting hepatocyte sheets. Once isolated, the hepatocytes were resuspended in hepatocyte growth media, seeded onto the wafer at a density of $111.3 \times 10^3$ cells/cm², and cultured at 5% $CO_2$ and 37° C. Cell attachment and growth was observed daily using microscopy and cell lifting occurred spontaneously.

After determining which method for culturing was best for lifting the hepatocytes and endothelial cells in an intact layer, both membranes were fixed in 10% buffered formalin for 1 hr and harvested for histological study, and the hepatocytes were stained immunohistochemically.

Immunohistochemical Staining. The hepatocyte cell monolayer membrane was fixed in 10% buffered formalin and processed for hematoxylin-eosin and immunohistochemical staining using a labeled streptavidin biotin method (LSAB2 kit for rat specimen, DAKO, Carpinteria, Calif., USA). The primary antibody was rabbit anti-albumin (ICN, Costa Mesa, Calif., USA). Three-micron sections were prepared and deparafinized. The specimens were treated with peroxidase blocking buffer (DAKO) to prevent the nonspecific staining. Sections were stained with albumin diluted with phosphate buffered saline, followed by biotinylated anti-rabbit antibody and HRP conjugated streptavidin. Sections were treated with DAB as substrate and were counterstained with hematoxylin.

Figure 18:
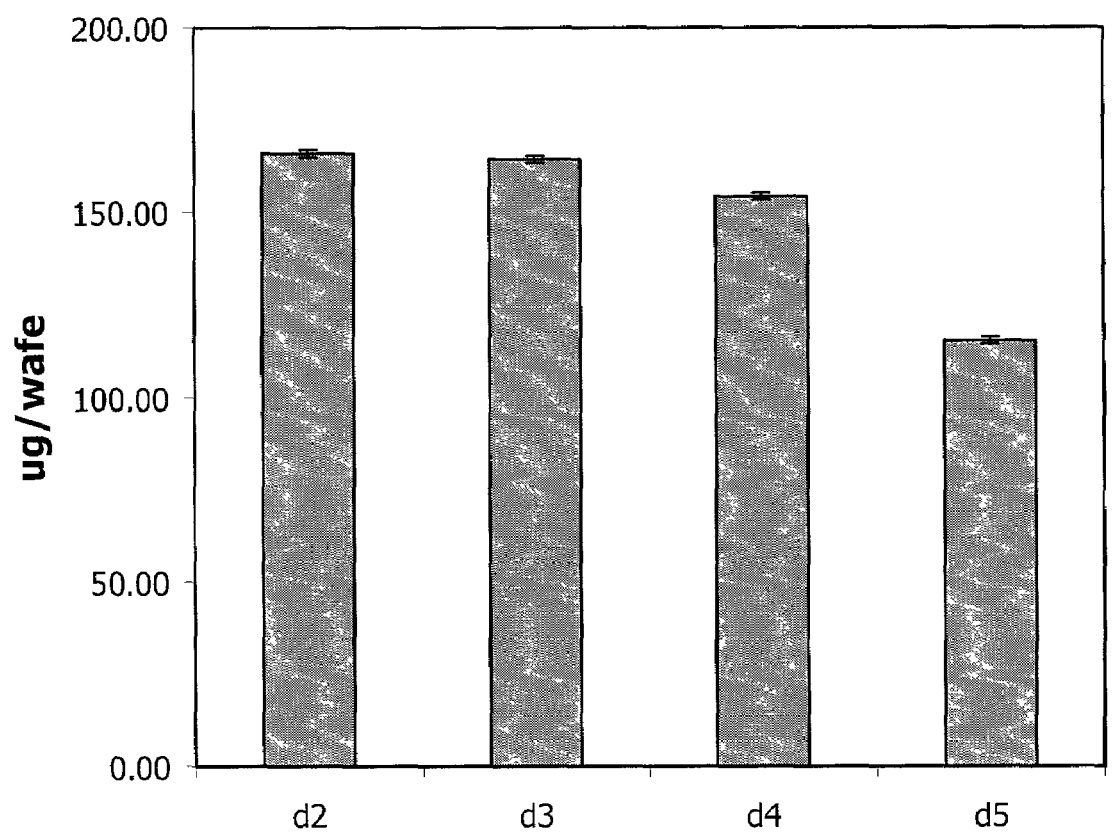
FIG. 18 is a set of bar graphs showing continued albumin production by hepatocyte cells cultured in a polymeric device of the invention. Albumin concentration in culture medium was measured every 24 hours for 5 days pre-cell detachment using an enzyme linked immunosorbent assay. No significant differences were observed between day 2, day 3, and day 4 ($p<0.05$ by the paired t-test).
Figure 19:
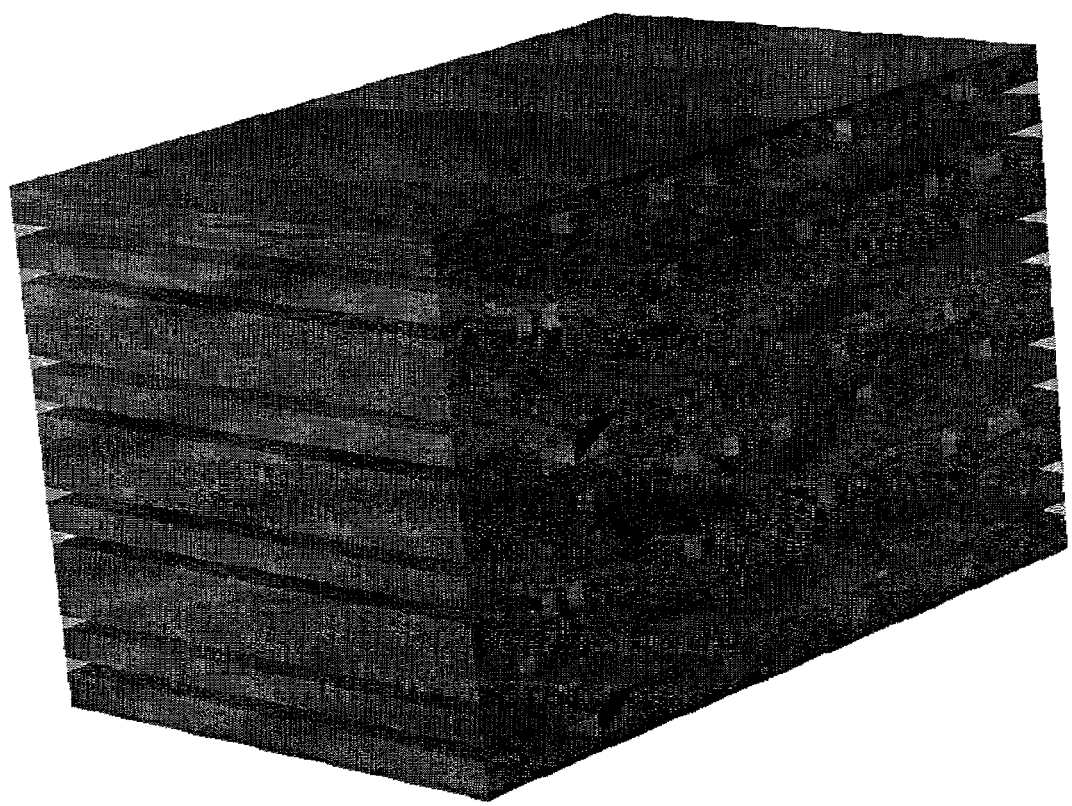
FIG. 19 is an image that shows the striated nature of an embodiment. Pores and channels appear in each layer, to transmit nutrients and oxygen. The gray (thicker) layers with the larger pores and channels provide support for hepatic cells and the formation of bile ducts. The dark gray (medium thickness) layers with the smaller pores and channels provide support for the cells of the vascular supply and the formation of blood vessels. The layers with pores and channels are separated by unpatterned pieces (light gray, thinner).
Figure 20:
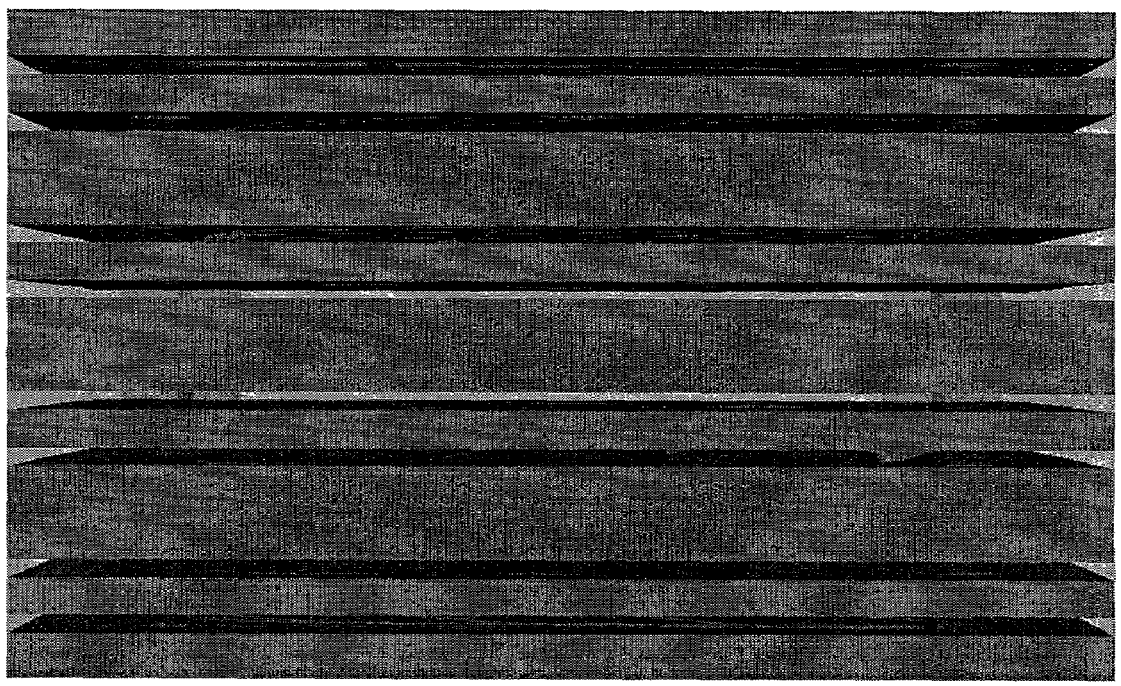
FIG. 20 is a side view of the embodiment of the invention shown in FIG. 19.
Figure 21:
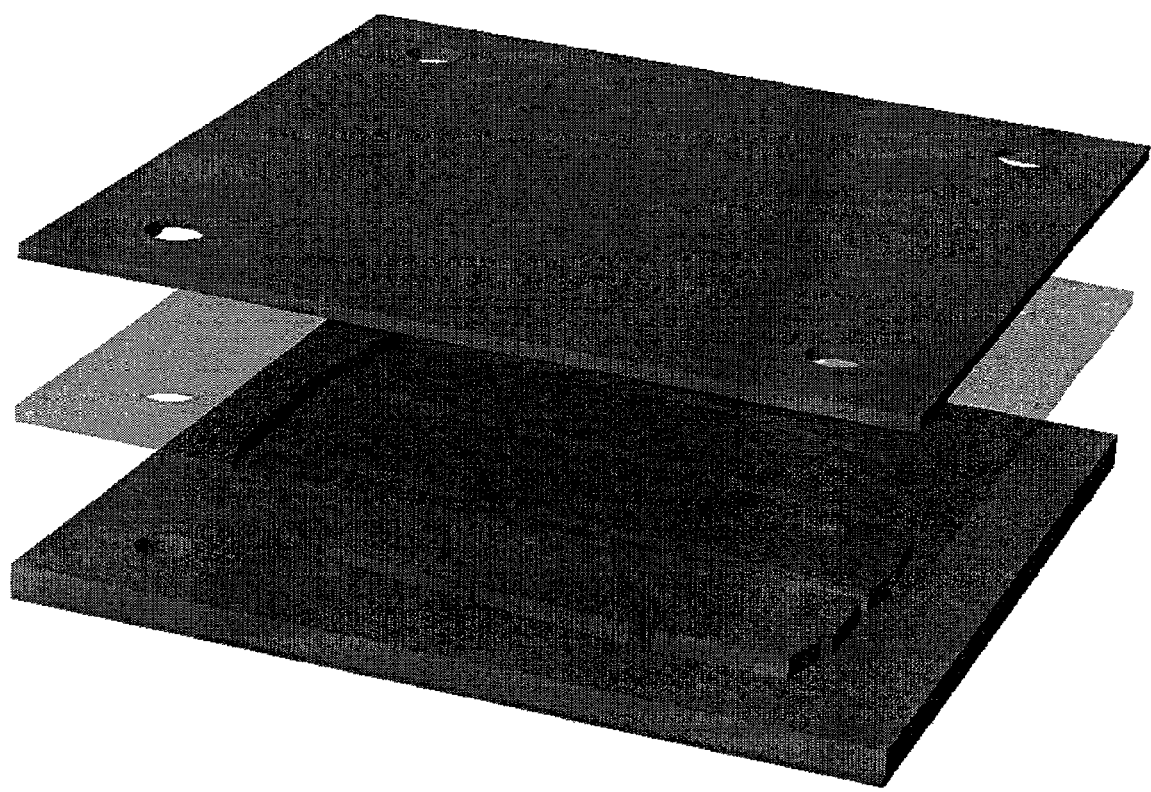
FIG. 21 shows an exploded view of the embodiment of the invention shown in FIG. 19. The top (dark gray, medium thickness) layer provides support for the cells of the vascular supply. The bottom (light gray, thinner) layer with the visible pores and channels provides support for hepatic cells. The middle (light gray) layer is an unpatterned piece.
Figure 22:
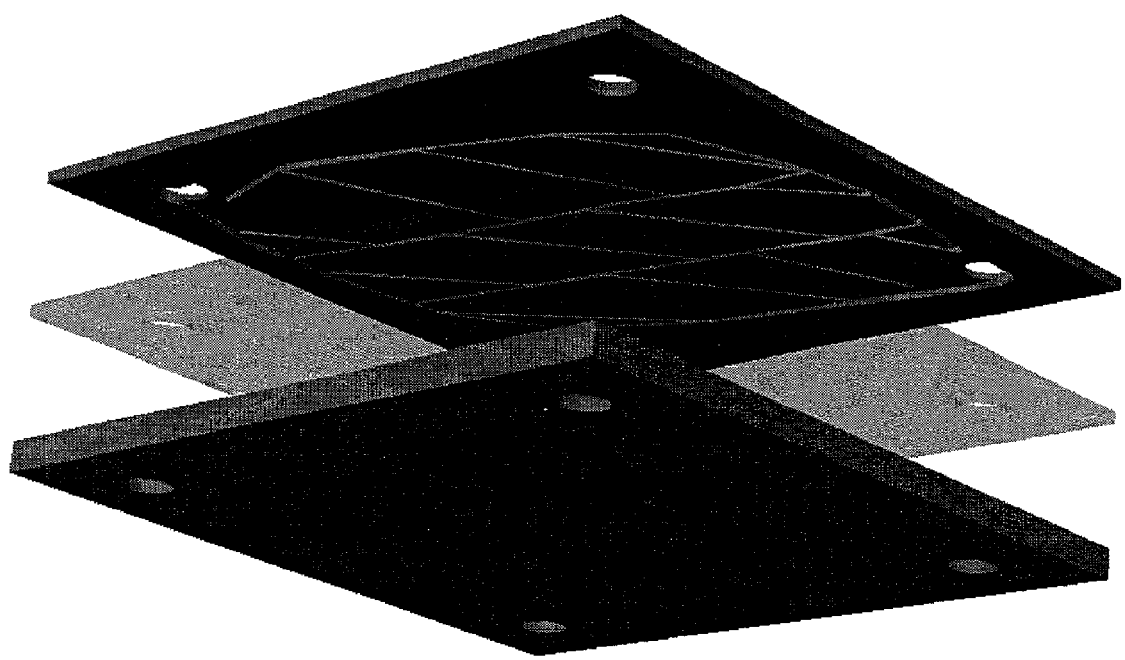
FIG. 22 shows another exploded view of the embodiment of the invention shown in FIG. 19. The top (dark gray, medium thickness) layer with the visible pores and channels provides support for the cells of the vascular supply. The bottom (gray, thicker) layer provides support for hepatic cells. The middle (light gray, thinner) layer is an unpatterned piece.

Albumin Production. To assess hepatocyte function, albumin concentration in the culture medium was measured every 24 hours for 5 days pre-cell detachment using an enzyme linked immunosorbent assay (n=5). In brief, a 96-well microplate was coated with anti-rat albumin antibody (ICN). After blocking non-specific responses with a 1% gelatin solution, each sample was seeded onto the plate and incubated for 1 hour. This was followed by another 1-hour incubation with peroxidase conjugated anti-rat albumin antibody (ICN). Finally, the substrate was added and extinction was measured with a microplate reader at 410 nm. $R^2$ of the standard curve was >0.99. Results are in FIG. 18, showing continued production of albumin by cultured hepatocytes.

Statistical Analysis. All data was expressed as mean ±SD. Statistical analysis was performed with Mann-Whitney's U test or Wilcoxon signed-rank test. When the p value of each test was less than 0.05, we judged it to be statistically significant.

Cell Attachment to Etched Silicon and Pyrex® Wafers. Endothelial cells and hepatocytes were also seeded onto etched silicon and Pyrex® wafers. Prior to cell seeding, the Pyrex® wafers were sterilized with 70% ethanol overnight and washed three times with sterile phosphate buffered saline (Gibco BRL). Silicon wafers were first soaked in acetone for 1 hr, followed a methanol rinse for 15 minutes, and overnight sterilization in 100% isopropyl alcohol. Onto these wafers were seeded rat lung microvascular endothelial cells at a density of $26.7 \times 10^3$ cells/cm², or rat hepatocytes at a density of $111.3 \times 10^3$ cells/cm². These cells were cultured at 5% $CO_2$ and 37° C., and their attachment and growth observed daily using microscopy.

Implantation of Hepatocyte Sheets into the Rat Omentum. Adult, male Lewis rats were treated with retrosine for over six weeks, a chemical that prevents natural liver regeneration, and portacaval shunt was created to direct any growth nutrients towards the omentum. Next, a thin layer of hepatocytes grown on and lifted from the non-etched silicon wafer implanted onto the omentum and a 70% partial hepatectomy was performed.

Results. We assessed the adhesion and growth of endothelial cells and hepatocytes on several different substrate surfaces. On all Pyrex® wafers, coated or non-coated, the endothelial cells proliferated and grew to confluence within four days. These cells did not lift spontaneously, and when scrapped, did not lift as a single sheet. In addition, when the non-coated silicon wafers were seeded with endothelial cells, the cell sheet fragmented upon lifting.

On the other hand, endothelial cells seeded onto silicon surfaces coated with vitrogen (30 g/ml), Matrigel® (1%), and gelatin (10 mg/ml) did lift with the use of mechanical means (i.e. a cell scrapper), and provided an intact monolayer sheet of endothelial cells. Upon observation, there were no significant differences in the effects of the three coatings on the detached cell sheets.

Hepatocytes also attached and spread well on all coated and non-coated Pyrex® wafers, and did not lift spontaneously or in sheets when scrapped after several days of growth. However, when seeded onto silicon wafers, they lifted spontaneously on all the non-coated and coated wafers. The hepatocyte sheets lifted from the non-coated wafers after 3 days, but the sheets were very fragile and fragmented easily. The monolayers that lifted from the thin and thickly coated vitrogen substrates (30 μg/ml and 3 μg/ml) lifted after 4 days in culture to form an intact hepatocyte layer. Cells lifted from the Matrigel® (1%) coated silicon wafers after 5 days in culture. There were no significant differences in appearance between the cell sheets lifted from the vitrogen and Matrigel® coated wafers.

Histological assessment of the detached cell monolayers of both hepatocytes and endothelial cells manifested promising results. Hematoxylin and eosin (H&E) staining of both showed that all cells were viable and that most were undergoing mitoses. The main difference, however, was in their patterning with one another; the endothelial cells were observed to be primarily attenuated and to form a predominant single-celled alignment. The hepatocytes, on the other hand, demonstrated very little of this marked tendency. Of the hepatocytes that did manifest a single-celled monolayeric alignment with one another, they were observed mophologically to more rounded and bulged. Both these results are similar to each of the cell types' specific functions: in biological systems, the endothelium functions to provide a thin, smooth outer surface. Thus, it is understandable that these cells are observed here to be primarily attentuated and in a single-celled array; because the hepatocytes have a more of tendency to form tissue. Hence, we see a less of a single-celled array and more of a rounded multilayered array, as shown in this EXAMPLE.

After one month, histological analysis and immunohistochemical staining have demonstrated the growth and proliferation of the hepatocyte sheet.

This EXAMPLE involves making a coherent structure over a broad range of scale. The channels begin as a single channel with a diameter of 500 μm, branch through 4 generations following a geometric scaling law which halves the channel width for each successive generation, form an array of capillary channels 10 microns in diameter, and then sequentially branch back to a single outflow vein. We have demonstrated that not only can we form the channels in silicon and Pyrex®, but that living endothelial cells will line the channels. In other experiments, we have demonstrated that cells on surfaces of silicon and Pyrex® will lay down matrix and form sheets of tissue of the cell type of origin, either hepatic or endothelial. We have also demonstrated the ability to peel these sheets from the surface and form three-dimensional units of tissue. In effect, the wafer of silicon or Pyrex® has acted as a mold for the formation of tissue.

EXAMPLE 2

Endothelialized Microvascular Networks Grown on Micromachined PYREX® Templates for Tissue Engineering of Vital Organs This EXAMPLE shows the design, modeling, and experimental/computational testing of the endothelialized microvascular matrices grown on micromachined Pyrex® templates.

Patterns of microvascular networks were etched using microfabrication technologies on Pyrex® wafers. The pattern consisted of 10 generations of bifurcations from a single inflow channel of width 3 mm down to channels of width of 30 microns.

The channels were then collected to a single outflow. All channels were etched to the same depth of 30 microns. The Pyrex® wafer was sealed to a flat silicone rubber sheet of the same size. Endothelial cells harvested from rat lung were successfully seeded and expanded under continuous flow conditions in this microvascular network. Red blood cells harvested from rat were heparinized and perfused into the endothelialized channels, and successfully collected at the output. Using micro-visualization techniques, the concentration of red blood cells (hematocrit) in the microvascular network was measured. The distribution of blood flow rate, pressure, and hematocrit was also calculated in the entire microvascular system using an earlier developed computational algorithm.

Epithelial cells were observed flowing through channels and attaching mainly around the walls of smallest channels on day 1 and growing to confluence along the channels under continuous flow conditions over the following 5 days. Rat lung endothelial cells attach in a single layer to the walls of these structures without occluding them.

Hematocrit compared well between the experimental measurements and numerical calculations. Red blood cells reach even the smallest vessels in the network, ensuring sustained transport of oxygen to the engineered capillaries.

In summary, microfabrication technology is demonstrated as an approach for organizing endothelial cells in vitro at the size scale of the microcirculation.

EXAMPLE 3

Microfluidics Device for Tissue Engineering Microvasculature: Endothelial Cell Culture In this EXAMPLE, we have focused on fabrication of the microfluidic scaffold, in vitro seeding, and extended cell culture in the device. Capillary networks were fabricated in biocompatible PDMS, sterilized, coated with cell adhesion molecules, and seeded with cells. Cell-containing devices were then connected to a closed-loop bioreactor for long-term culture. We have used the device to demonstrate continuous-flow culture of endothelial cells for up to 4 weeks without occlusion or contamination.

In this EXAMPLE using confined geometries, we used traditional soft lithography microfluidics as a prototype matrix. These cell-containing microfluidics is capable of supporting long-term culture in vitro, because in vitro expansion of cells prior to implantation can take weeks. The prototype matrix is designed to supply sufficient oxygen and nutrients while avoiding large shear stresses. The matrix is useful for long-term microfluidic cell culture, including the maintenance of sterility and the minimization of cell and bubble occlusions.

We have developed microfluidic networks that support physiologic flows and pressures by photopatterning SU-8, a high-aspect ratio negative photoresist, onto silicon. This is used as a mold for casting polydimethylsiloxane (PDMS). After removal from the mold, inlets and outlets are cored with blunted syringe needles, and the micropatterned polymer is irreversibly sealed to an unpatterned layer of Pyrex® or PDMS by oxygen plasma surface treatment. See, Duffy D C et al., *Anal. Chem.* 70, 4974-4984 (1998). The microfluidic device is autoclave sterilized and perfused with a solution containing cell adhesion molecules (poly-L-lysine, collagen, gelatin, or fibronectin), which are allowed to adsorb for one hour.

The fluidic network is then seeded with a $1\times10^6$-$1\times10^8$ cells/mL cell suspension using a syringe pump at flow rates ranging from 10-100 µL/min. The cells are then allowed to attach for 24 hours, after which the device is connected in-line with a sterile bioreactor consisting of a peristaltic pump, oxygenator, bubble trap, and a reservoir of sterile culture medium. Sterile culture medium is pumped peristaltically from a sterile reservoir through an oxygenator consisting of a long length of tubing semipermeable to oxygen. The oxygenator is followed by a small bubble trap, and leads directly to the microfluidic circuit. Finally, the system is run closed-loop in an incubator at standard culture settings.

Autoclave sterilization of the microfluidic circuit caused no obvious pattern distortion. Coating the channels with cell adhesion molecules enhanced cell attachment when compared to phosphate buffered saline coated control channels. Seeding of cells into channels of widths between 30-200 µm was optimized by varying concentrations and flow rates. The continuous-flow bioreactor was used to dynamically culture endothelial cells at flow rates between 0.01 mL/min and 0.1 mL/min. Both single channels and complex networks of channels (30-200 µm wide and 40 µm deep) were successfully seeded and cultured. In 100 µm×40 µm single channels, cells have been cultured for more than 4 weeks without contamination or occlusion.

While cells have previously been introduced into microchannels for sorting or analysis purposes, they had not been cultured long term in microfluidic devices. However, in this EXAMPLE, we have successfully seeded and cultured endothelial cells in microfabricated channels for 4 weeks, demonstrating that cells successfully attach, proliferate, and migrate in closed channels with small geometries.

EXAMPLE 4

Microfabrication of Biodegradable Polymer Scaffolds and Microfluidics for Tissue Engineering In this EXAMPLE, we use of microfabrication to develop an implantable fully biodegradable microdevice. We use processes specifically developed for fabricating, micropatterning, and bonding films of the commonly used biodegradable polymer Poly-lactic-co-glycolic acid PLGA. We demonstrate the use of these processes to build a degradable microfluidic circuit that will be used to provide guidance of endothelial cells in the development of artificial microvasculature to support the tissue engineering of bulk organs.

Micropatterned molds are fabricated using DRIE with a terminal polymer passivation step to aid release of polymer casts. The silicon pattern is then transferred to a PDMS elastomer which acts as a mold for degradable polymer patterning. PLGA is compression molded on the PDMS mold at 100-130° C. for 15 minutes. At this temperature, the polymer is a viscous melt and conforms to the mold, resulting in nearly perfect pattern translation. During this step, the thickness of the film is controlled by the applied compressive force. The process is capable of achieving films as thin as 200 µm with resolution of 2 µm, as demonstrated by microscopic observation a series of parallel lines and space. The patterns are preserved with great integrity after processing.

Bonding the micropatterned degradable films is accomplished when PLGA films are brought into contact above their glass transition temperature. Interdiffusion of the polymer chains across the interface is used to control the strength of bonding of similar polymer films as predicted by reptation theory. Guided by this model, we promote the temperature dependent interdiffusion process by placing films in intimate contact in an oven at 55° C. for 20-60 minutes (times vary due to differences in film flatness). The process ceiling (maximum time and temperature) is dominated by pattern deformation resulting from viscous flow of polymer (~24 hours for 300 µm×40 µm channels at 55° C.). Because fusion bonding takes place on a time scale much smaller than pattern deformation, a large process window results which will be critical for the formation of high aspect ratio (large width and shallow depth) channels.

The processes we describe here require minimal equipment, because the molds are reusable. The process takes approximately 1 hour once molds are fabricated, and so can be used for rapid prototyping. The processes are highly reproducible, and can readily be applied to diverse applications in in vivo biology and medicine. We have demonstrated their use to fabricate fully biodegradable implantable microfluidic networks capable of supporting physiologic flows and pressures.

The foregoing description has been presented only for the purposes of illustration and is not intended to limit the invention to the precise form disclosed, but by the claims appended hereto.

We claim:

1. A multilayer device for use in tissue engineering, comprising:
    (a) at least a first layer comprised of a polymer scaffold having a pattern of microchannels therein and
        (i) wherein the microchannels are suitable for the attachment and culturing of animal cells within the microchannels, and
        (ii) wherein the microchannels are connected for the circulation of fluid through the first layer, and
    (b) at least a second layer comprised of a polymer scaffold,
wherein the first and second layers are joined or fastened together and the first layer is formed by forming a mold from a substrate material using a photoresist processing technique that includes: i) coating the substrate material with a photoresist; and ii) forming a pattern in the photoresist, and casting the first layer on the respective mold.

2. The multilayer device of claim 1, wherein the polymer of the first layer is biodegradeable.

3. The multilayer device of claim 1, wherein the polymers of all the layers of the multilayer device are biodegradable.

4. The multilayer device of claim 1, wherein the second layer has a pattern of microchannels therein.

5. The multilayer device of claim 4, wherein the pattern in the first and second layers are similar.

6. The multilayer device of claim 4, wherein the pattern in the first and second layers are different.

7. The multilayer device of claim 4, wherein the pattern in the first layer is suitable for the culturing of endothelial cells and the layer in the second layer is suitable for the culturing of parenchymal cells.

8. The multilayer device of claim 4, wherein the patterns of the first and second layers are aligned to form a vasculature.

9. The multilayer device of claim 1, wherein the channels of the first layer are connected beginning from one or more inlets, expanding into more channels, and then converging back into one or more outlets.

10. The multilayer device of claim 1, wherein the channels of all the layers of the multilayer device are connected beginning from one or more inlets, expanding into more channels, and then converging back into one or more outlets.

11. The multilayer device of claim 1, further comprising a third layer comprised of a micromachined polymer scaffold suitable for attachment and culturing of animal cells, wherein the first, second and third layers are joined or fastened together.

12. The multilayer device of claim 11,
    (a) wherein the second layer is unpatterned; and
    (b) wherein the third layer has a pattern of channels therein,
        (i) wherein the channels are suitable for the attachment and culturing of animal cells within the channels, and
        (ii) wherein the channels are connected for the circulation of fluid through the layer.

13. The multilayer device of claim 12, wherein the pattern in the first and third layers are similar.

14. The multilayer device of claim 12, wherein the pattern in the first and third layers are different.

15. The multilayer device of claim 14, wherein the pattern in the first layer is suitable for the culturing of endothelial cells and the layer in the third layer is suitable for the culturing of parenchymal cells.

16. The multilayer device of claim 1, wherein the animal cells are selected from the group consisting of endothelial cells, parenchymal cells, bone marrow cells, osteoblasts, mesenchymal stem cells, satellite cells, and fibroblasts.

17. The multilayer device of claim 1, wherein the cells cultured in the channels of the first layer are endothelial cells.

18. The multilayer device of claim 1, wherein one or more of the layers comprise through-holes.

19. The multilayer device of claim 1, wherein one or more of the layers comprise an alignment indentation on the surface of a layer and an alignment protrusion on an opposing surface of a layer, the alignment indentations shaped to mate with the alignment protrusion.

20. The multilayer device of claim 1, wherein the first layer is subdivided into zones of animal cell support.

21. The multilayer device of claim 20, wherein the zones of animal cell support comprise cell adhesion molecules.

22. The multilayer device of claim 7 or 15, wherein the pattern in the first layer comprises microchannels that are about 30-200 microns in width.

23. The multilayer device of claim 1, wherein the substrate is selected from the group consisting of silicon, ceramic, and glass.

24. The multilayer device of claim 1, wherein the second layer is formed by forming a mold from a substrate selected from the group consisting of silicon, ceramic, and glass using a photoresist processing technique, and casting the second layer on the respective mold, wherein the photoresist processing technique for the second layer includes coating the substrate with a photoresist, forming a pattern in the photoresist to form a second mold and casting the second layer on the second mold.

25. The multilayer device of claim 24, wherein the molds for the first and second layers are the same.

26. The multilayer device of claim 24, wherein the molds for the first and second layers are different.

27. The multilayer device of claim 1, wherein the polymer scaffold is selected from a material consisting of a biocompatible material, a biodegradable material, a porous material, a non-porous material and combinations thereof.

28. The multilayer device of claim 1, wherein the microchannels are a branched pattern.

29. The multilayer device of claim 1, wherein the microchannels have a height and width of about 30-200 microns.

30. The multilayer device of claim 1, wherein the photoresist in combination with the substrate material form the mold.

31. The multilayer device of claim 1, wherein forming the mold includes etching the substrate.

32. The multilayer device of claim 1, wherein forming the mold includes etching the substrate in a pattern exposed through the photoresist and stripping the photoresist therefrom.

33. The multilayer device of claim 1, wherein the photoresist processing technique further includes the step of etching the pattern into the substrate.

34. A multilayer device for use in tissue engineering, comprising:
(a) at least a first layer comprised of a polymer scaffold having a pattern of microchannels therein and
  (i) wherein the microchannels are suitable for the attachment and culturing of animal cells within the microchannels,
  (ii) wherein the microchannels are connected for the circulation of fluid through the first layer, and
  (iii) wherein the at least a first layer is fabricated by forming a mold from a semiconductor substrate material using a photoresist processing technique that includes coating the semiconductor substrate material with a photoresist, and forming a pattern in the photoresist, and then casting the at least a first layer on the mold; and
(b) at least a second layer comprised of a polymer scaffold, wherein the first and second layers are joined or fastened together.

35. A method of making a multilayer device, comprising the steps of:
(a) fabricating at least a first layer comprised of a polymer scaffold suitable for attachment and culturing of animal cells and having a pattern of channels therein, wherein the at least a first layer is fabricated by forming a mold from a semiconductor substrate material using a photoresist processing technique that includes coating the semiconductor substrate material with a photoresist, and forming a pattern in the photoresist, and then casting the at least a first layer on the mold, and
  (i) wherein the channels are suitable for the attachment and culturing of animal cells within the channels,
  (ii) wherein the channels are connected for the circulation of fluid through the layer, and
  (iii) wherein at least one of the channels is about 30-200 microns in width;
(b) obtaining at least a second layer for supporting animal cell growth wherein the second layer is comprised of a polymer scaffold suitable for attachment and culturing of animal cells; and
(c) fastening together the first and second layers to form lumens of the channels.

36. The method of claim 35, wherein the joining or fastening is by a method selected from the group consisting of the methods of solvent bonding; reflow by heating; treating the surface of the layer with oxygen plasma; polymer flow at the surface of the layer, mechanically fastening the layers with fasteners selected from the group comprising barbs, pins, screws, clamps, staples, wires, string, and sutures; and adhering the layers by the use of adhesives, adhesive films or adhesive layers.

37. The method of claim 35, wherein the lumens are substantially rectangular.

38. A method of making a multilayer device comprising the steps of:
(a) obtaining layers of a multilayer device, comprising:
  (i) at least a first layer comprised of a polymer scaffold having a pattern of microchannels therein, and
    (A) wherein the pattern of microchannels are suitable for the attachment and culturing of animal cells within the channels,
    (B) wherein the pattern of microchannels are connected for the circulation of fluid through the layer; and
    (C) wherein the first layer is formed by forming a first mold from a substrate material using a photoresist processing technique that includes coating the substrate material with a photoresist, and forming a pattern in the photoresist, and then casting an elastomer on the mold such that the pattern in the photoresist is transferred to the elastomer which acts as a second mold for the first layer, and
  (ii) at least a second layer, wherein the second layer is comprised of a polymer scaffold for attachment and culturing of animal cells; and
(b) fastening the at least a first layer and the at least a second layer together.

39. The method of claim 38, wherein the animal cells are selected from the group consisting of endothelial cells, parenchymal cells, bone marrow cells, osteoblasts, mesenchymal stem cells, satellite cells, and fibroblasts.

40. The method of claim 38, further comprising the step of (c) seeding animal cells to into the channels.

41. The method of claim 38, wherein the animal cells are endothelial cells.

42. The method of claim 38, wherein the first layer is compression molded on the mold.

43. The method of claim 38, wherein the polymer scaffold is about 200 microns thick.

44. The method of claim 38, wherein the microchannels are about 2 microns in width.

45. The method of claim 38, further comprising the steps of implanting the multilayer device and seeding animal cells onto at least the first layer.

46. The method of claim 38, wherein the elastomer is a polydimethylsiloxane elastomer.

47. A method of implanting a bioartificial organ into a recipient, comprising:
(a) obtaining a multilayer device, comprising:
  (i) at least a first layer comprised of a polymer scaffold having a pattern of microchannels therein, and
    (A) wherein the microchannels are suitable for the attachment and culturing of animal cells within the channels,
    (B) wherein the microchannels are connected for the circulation of fluid through the layer, and
    (C) wherein the first layer is formed by forming a mold from a semiconductor substrate material using a photoresist processing technique that includes coating the semiconductor substrate material with a light sensitive photoresist, and forming a pattern in the photoresist by exposing the photoresist to short-wavelength light through a semi-transparent mask to create a microfluidic pattern in the photoresist, and then casting the first layer on the mold, and removing the first layer from the mold; and (ii) at least a second layer wherein the second layer is comprised of a polymer scaffold, the layers of the multilayer device being fastened together; and (b) implanting the multilayer device into the recipient, wherein the implanted multilayer device is a bioartificial organ.

48. The method of claim 47, wherein the multilayer device is seeded with animal cells.

49. The method of claim 48, wherein the multilayer device is seeded with animal cells after implanting.

50. A method as recited in claim 47, further comprising the step of etching the pattern of microchannels in the substrate.

* * * * *